United States Patent
Shelton, IV et al.

(10) Patent No.: US 11,896,226 B2
(45) Date of Patent: Feb. 13, 2024

(54) COMPRESSIBLE ADJUNCTS WITH HEALING-DEPENDENT DEGRADATION PROFILE

(71) Applicant: Cilag GmbH International, Zug (CH)

(72) Inventors: Frederick E. Shelton, IV, Hillsboro, OH (US); Michael J. Vendely, Lebanon, OH (US)

(73) Assignee: Cilag GmbH International, Zug (CH)

(*) Notice: Subject to any disclaimer, the term of this patent is extended or adjusted under 35 U.S.C. 154(b) by 390 days.

(21) Appl. No.: 17/217,680

(22) Filed: Mar. 30, 2021

(65) Prior Publication Data

US 2022/0313260 A1    Oct. 6, 2022

(51) Int. Cl.
*A61B 17/072* (2006.01)
*A61K 9/00* (2006.01)
*A61B 17/00* (2006.01)

(52) U.S. Cl.
CPC ...... *A61B 17/07292* (2013.01); *A61K 9/0024* (2013.01); *A61B 2017/00004* (2013.01);
(Continued)

(58) Field of Classification Search
CPC ............ A61B 17/07292; A61B 9/0024; A61B 2017/00004; A61B 2017/00884;
(Continued)

(56) References Cited

U.S. PATENT DOCUMENTS 5,711,960 A   1/1998 Shikinami
5,833,695 A   11/1998 Yoon
(Continued)

FOREIGN PATENT DOCUMENTS

EP   2113206 A2   11/2009
EP   2333701 A1   6/2011
(Continued)

OTHER PUBLICATIONS

U.S. Appl. No. 17/217,252, filed Mar. 30, 2021, Method for Treating Tissue.
(Continued)

*Primary Examiner* — Julian W Woo
(74) *Attorney, Agent, or Firm* — Lisa Adams

(57) ABSTRACT

A compressible adjunct for use with a staple cartridge is provided and includes a biocompatible adjunct material configured to be releasably retained on a staple cartridge and configured to be delivered to tissue by deployment of staples in the staple cartridge. The adjunct material is formed from a porous polymer body and is configured to exhibit a first stiffness in compression that is approximately constant during a first time period from contact with the tissue. The adjunct material is further configured to exhibit a second stiffness in compression during a second time period following the first time period. The second stiffness is less than the first stiffness and is configured to decrease with time as a function of at least one of oxidation, enzyme-catalyzed hydrolysis, and change of pH resulting from interaction with at least one physiological element released from the tissue during healing progression of the tissue.

9 Claims, 14 Drawing Sheets

(52) U.S. Cl.
CPC .............. *A61B 2017/00884* (2013.01); *A61B 2017/00893* (2013.01); *A61B 2017/00942* (2013.01); *A61B 2017/07257* (2013.01); *A61B 2017/07271* (2013.01); *A61B 2017/07285* (2013.01)

(58) Field of Classification Search
CPC  A61B 2017/00893; A61B 2017/00942; A61B 2017/00938; A61B 2017/00964
See application file for complete search history.

(56) References Cited

U.S. PATENT DOCUMENTS

| | | | |
|---|---|---|---|
| 6,029,671 A | 2/2000 | Stevens et al. | |
| 7,143,925 B2 | 12/2006 | Shelton, IV et al. | |
| 7,601,118 B2 | 10/2009 | Smith et al. | |
| 8,062,330 B2 | 11/2011 | Prommersberger et al. | |
| 8,317,070 B2 | 11/2012 | Hueil et al. | |
| 8,393,514 B2 | 3/2013 | Shelton, IV et al. | |
| 8,752,699 B2 * | 6/2014 | Morgan ................ | A61B 17/29 606/220 |
| 8,864,007 B2 | 10/2014 | Widenhouse et al. | |
| 9,084,602 B2 | 7/2015 | Gleiman | |
| 9,232,941 B2 | 1/2016 | Mandakolathur et al. | |
| 9,272,406 B2 | 3/2016 | Aronhalt et al. | |
| 9,282,962 B2 | 3/2016 | Schmid et al. | |
| 9,480,476 B2 | 11/2016 | Aldridge et al. | |
| 9,681,936 B2 | 6/2017 | Hodgkinson et al. | |
| 9,913,642 B2 | 3/2018 | Leimbach et al. | |
| 9,999,408 B2 | 6/2018 | Boudreaux et al. | |
| 10,111,661 B2 | 10/2018 | Widenhouse et al. | |
| 10,136,890 B2 | 11/2018 | Shelton, IV et al. | |
| 10,136,891 B2 | 11/2018 | Shelton, IV et al. | |
| 10,166,023 B2 | 1/2019 | Vendely et al. | |
| 10,172,611 B2 | 1/2019 | Shelton, IV et al. | |
| 10,172,617 B2 | 1/2019 | Shelton, IV et al. | |
| 10,172,618 B2 | 1/2019 | Shelton, IV et al. | |
| 10,251,649 B2 | 4/2019 | Schellin et al. | |
| 10,258,332 B2 | 4/2019 | Schmid et al. | |
| 10,265,091 B2 | 4/2019 | Nativ et al. | |
| 10,285,692 B2 | 5/2019 | Widenhouse et al. | |
| 10,314,588 B2 | 6/2019 | Turner et al. | |
| 10,349,939 B2 | 7/2019 | Shelton, IV et al. | |
| 10,368,869 B2 | 8/2019 | Olson et al. | |
| 10,433,846 B2 | 10/2019 | Vendely et al. | |
| 10,517,592 B2 | 12/2019 | Shelton, IV et al. | |
| 10,548,593 B2 | 2/2020 | Shelton, IV et al. | |
| 10,568,621 B2 | 2/2020 | Shelton, IV et al. | |
| 10,569,071 B2 | 2/2020 | Harris et al. | |
| 10,588,623 B2 | 3/2020 | Schmid et al. | |
| 10,772,732 B1 | 9/2020 | Miller et al. | |
| 10,939,911 B2 | 3/2021 | Huitema et al. | |
| 11,116,505 B2 | 9/2021 | Vendely et al. | |
| 11,224,423 B2 | 1/2022 | Shelton, IV et al. | |
| 11,291,449 B2 | 4/2022 | Swensgard et al. | |
| 11,406,377 B2 | 8/2022 | Schmid et al. | |
| 11,504,125 B2 | 11/2022 | Shelton, IV et al. | |
| 11,602,341 B2 | 3/2023 | Shelton, IV et al. | |
| 11,627,961 B2 | 4/2023 | Shelton, IV et al. | |
| 11,707,278 B2 | 7/2023 | Vadali et al. | |
| 2002/0014951 A1 | 2/2002 | Kramer et al. | |
| 2004/0101546 A1 | 5/2004 | Gorman et al. | |
| 2004/0101548 A1 | 5/2004 | Pendharkar | |
| 2005/0070929 A1 | 3/2005 | Dalessandro et al. | |
| 2007/0021760 A1 | 1/2007 | Kelleher | |
| 2007/0034669 A1 | 2/2007 | De et al. | |
| 2007/0179528 A1 | 8/2007 | Soltz et al. | |
| 2007/0251835 A1 | 11/2007 | Mika et al. | |
| 2008/0051866 A1 | 2/2008 | Chen et al. | |
| 2009/0093550 A1 | 4/2009 | Rolfes et al. | |
| 2009/0123517 A1 | 5/2009 | Flanagan et al. | |
| 2009/0206142 A1 | 8/2009 | Huitema et al. | |
| 2009/0209031 A1 | 8/2009 | Stopek | |
| 2010/0331880 A1 | 12/2010 | Stopek | |
| 2012/0100200 A1 | 4/2012 | Belcheva et al. | |
| 2012/0241491 A1 | 9/2012 | Aldridge et al. | |
| 2012/0241498 A1 | 9/2012 | Gonzalez et al. | |
| 2012/0289979 A1 | 11/2012 | Eskaros et al. | |
| 2013/0146643 A1 | 6/2013 | Schmid et al. | |
| 2013/0172929 A1 | 7/2013 | Hess et al. | |
| 2013/0209659 A1 | 8/2013 | Racenet et al. | |
| 2013/0221065 A1 | 8/2013 | Aronhalt et al. | |
| 2013/0256377 A1 | 10/2013 | Schmid et al. | |
| 2014/0155916 A1 | 6/2014 | Hodgkinson et al. | |
| 2014/0166726 A1 | 6/2014 | Schellin et al. | |
| 2014/0205637 A1 | 7/2014 | Widenhouse et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0136831 A1 | 5/2015 | Baxter, III et al. | |
| 2015/0196296 A1 | 7/2015 | Swayze et al. | |
| 2015/0238191 A1 | 8/2015 | Schellin et al. | |
| 2015/0297236 A1 | 10/2015 | Harris et al. | |
| 2015/0351761 A1 | 12/2015 | Shelton, IV et al. | |
| 2015/0351764 A1 | 12/2015 | Shelton, IV | |
| 2016/0100839 A1 | 4/2016 | Marczyk et al. | |
| 2016/0106427 A1 | 4/2016 | Shelton, IV et al. | |
| 2016/0345976 A1 | 12/2016 | Gonzalez et al. | |
| 2017/0049448 A1 | 2/2017 | Widenhouse et al. | |
| 2017/0055992 A1 | 3/2017 | Widenhouse et al. | |
| 2017/0055994 A1 | 3/2017 | Vendely et al. | |
| 2017/0056018 A1 | 3/2017 | Zeiner et al. | |
| 2017/0056567 A1 | 3/2017 | Harris et al. | |
| 2017/0119391 A1 | 5/2017 | Schellin et al. | |
| 2017/0281181 A1 | 10/2017 | Matonick et al. | |
| 2017/0296213 A1 | 10/2017 | Swensgard et al. | |
| 2018/0085124 A1 | 3/2018 | Nativ et al. | |
| 2018/0235613 A1 | 8/2018 | Shelton, IV et al. | |
| 2018/0235616 A1 | 8/2018 | Shelton, IV et al. | |
| 2018/0235625 A1 | 8/2018 | Shelton, IV et al. | |
| 2018/0353174 A1 | 12/2018 | Widenhouse et al. | |
| 2018/0353175 A1 | 12/2018 | Widenhouse et al. | |
| 2018/0353659 A1 | 12/2018 | Widenhouse et al. | |
| 2019/0200844 A1 | 7/2019 | Shelton, IV et al. | |
| 2019/0200981 A1 | 7/2019 | Harris et al. | |
| 2019/0201140 A1 | 7/2019 | Yates et al. | |
| 2019/0206004 A1 | 7/2019 | Shelton, IV et al. | |
| 2019/0206562 A1 | 7/2019 | Shelton, IV et al. | |
| 2019/0254654 A1 | 8/2019 | Shelton, IV et al. | |
| 2019/0254655 A1 | 8/2019 | Shelton, IV et al. | |
| 2019/0328390 A1 | 10/2019 | Harris et al. | |
| 2019/0344064 A1 | 11/2019 | Buchanan | |
| 2020/0205825 A1 | 7/2020 | Vendely et al. | |
| 2020/0238244 A1 | 7/2020 | Tchakalova et al. | |
| 2021/0077094 A1 | 3/2021 | Harris et al. | |
| 2021/0077109 A1 | 3/2021 | Harris et al. | |
| 2021/0346015 A1 | 11/2021 | Krulevitch et al. | |
| 2022/0313145 A1 | 10/2022 | Shelton, IV et al. | |
| 2022/0313245 A1 | 10/2022 | Shelton, IV et al. | |
| 2022/0313246 A1 | 10/2022 | Shelton, IV et al. | |
| 2022/0313255 A1 | 10/2022 | Shelton, IV et al. | |
| 2022/0313256 A1 | 10/2022 | Shelton, IV et al. | |
| 2022/0313257 A1 | 10/2022 | Shelton, IV et al. | |
| 2022/0313258 A1 | 10/2022 | Shelton, IV et al. | |
| 2022/0313259 A1 | 10/2022 | Shelton, IV et al. | |
| 2022/0313262 A1 | 10/2022 | Shelton, IV et al. | |
| 2022/0313874 A1 | 10/2022 | Shelton, IV et al. | |
| 2023/0158214 A1 | 5/2023 | Shelton, IV et al. | |

FOREIGN PATENT DOCUMENTS

| | | | |
|---|---|---|---|
| EP | 2395333 | A1 | 12/2011 |
| EP | 2604196 | A2 | 6/2013 |
| EP | 2628491 | A2 | 8/2013 |
| EP | 3132811 | A1 | 2/2017 |
| EP | 3530199 | A2 | 8/2019 |
| EP | 3756612 | A2 | 12/2020 |
| EP | 3782558 | A2 | 2/2021 |
| EP | 3791804 | A2 | 3/2021 |
| EP | 3791809 | A1 | 3/2021 |
| WO | 9824048 | A1 | 6/1998 |
| WO | 2006044490 | A2 | 4/2006 |

(56) References Cited

FOREIGN PATENT DOCUMENTS

| WO | 2006068999 A2 | 6/2006 |
|----|---------------|--------|
| WO | 2015187793 A1 | 12/2015 |
| WO | 2020021433 A1 | 1/2020 |
| WO | 2022079516 A1 | 4/2022 |

OTHER PUBLICATIONS

U.S. Appl. No. 17/216,977, filed Mar. 30, 2021, Compressible Adjuncts With Fluid Control Features.
U.S. Appl. No. 17/216,978, filed Mar. 30, 2021, Compressible Adjuncts With Drug.
U.S. Appl. No. 17/216,982, filed Mar. 30, 2021, Compressible Adjuncts With Drug Release Features.
U.S. Appl. No. 17/216,985, filed Mar. 30, 2021, Compressible Adjuncts With Drug.
U.S. Appl. No. 17/216,994, filed Mar. 30, 2021, Compressible Adjuncts With Different Behavioral Zones.
U.S. Appl. No. 17/216,914, filed Mar. 30, 2021, Smart Packaging for Tissue Adjuncts.
U.S. Appl. No. 17/216,946, filed Mar. 30, 2021, Passively Powered Packaging for Tissue Adjuncts.
U.S. Appl. No. 17/216,953, filed Mar. 30, 2021, Using Smart Packaging in Adjusting.
U.S. Appl. No. 17/216,960, filed Mar. 30, 2021, Monitoring Healing After Tissue.
U.S. Appl. No. 17/217,578, filed Mar 30, 2021, Implantable Adjuncts Having Adjustable Degradation Profile.
U.S. Appl. No. 17/217,736, filed Mar. 30, 2021, Tissue Thickness Compensating Adjuncts Having Regions of Differential Expansion.
U.S. Appl. No. 17/217,784, filed Mar. 30, 2021, Composite Adjuncts That Degrade Through Multiple Different Mechanisms.
International Patent Application No. PCT/IB2020/060710 entitled "Drug Delivery Device Sensing Modules", filed on Nov. 13, 2020, 100 pages.
U.S. Appl. No. 17/022,520 entitled "Method of Applying Buttress to End Effector of Surgical Stapler", filed Sep. 16, 2020, 226 pages.
U.S. Appl. No. 17/068,857 entitled "Adaptive Responses From Smart Packaging of Drug Delivery Absorbable Adjuncts", filed Oct. 13, 2020, 97 pages.
Agren et al. (Jul. 2006) "Action of Matrix Metalloproteinases at Restricted Sites in Colon Anastomosis Repair: An Immunohistochemical and Biochemical Study", Surgery, 140(1):72-82.
Aslanian et al. (Mar.-Apr. 1984) "Dietary Intake and Urinary Excretion of Various Mineral Substances in Patients with Hypertension and Ischemic Heart Disease", Vopr Pitan, (2):16-9(English Abstract).
Bezwada Rao S. (2008) "Controlled Release of Drugs from Novel Absorbable Oligomers and Polymers", White Paper, Bezwada Biomedical, 7 pages.
Bezwada Rao S. (2008) "Functionalized Triclosan for Controlled Release Applications", White Paper, AP Bezwada Biomedical, 6 pages.
Bezwada Rao S. (2010) "Nitric Oxide and Drug Releasing Hydrolysable Macromers, Oligomers and Polymers", Chapter 11 of Biomaterials, ACS Symposium Series, American Chemical Society: Washington, DC, 24 pages.
Bezwada Rao S. (Mar. 2009) "Nitric Oxide and Drug Releasing Hydrolysable Macromers, Oligomers and Polymers", White Paper, Bezwada Biomedical, 9 pages.
Bosmans et al. (2015) "Colorectal Anastomotic Healing: Why the Biological Processes that Lead to Anastomotic Leakage Should be Revealed Prior to Conducting Intervention Studies", BMC Gastroenterology, 15:180(6 pages).
Broughton et al. (Jun. 2006) "The Basic Science of Wound Healing", Plastic and Reconstructive Surgery, 117(7 Suppl):12S-34S.
Casalani et al. (Oct. 11, 2019) "A Perspective on Polylactic Acid-Based Polymers Use for Nanoparticles Synthesis and Applications", Frontiers in Bioengineering and Biotechnology, 7(259):1-16.

De Hingh et al. (Jun. 21, 2002) "The Matrix Metalloproteinase Inhibitor BB-94 Improves the Strength of Intestinal Anastomoses in the Rat", International Journal of Colorectal Disease, 17(5):348-354.
Fatouros et al. (Oct. 1999) "Influence of Growth Factors Erythropoietin and Granulocyte Macrophage Colony Stimulating Factor on Mechanical Strength And Healing of Colonic Anastomoses in Rats", The European Journal of Surgery, 165(10):986-992.
Gibson et al. (Nov. 2009) "MMPs Made Easy", Wounds International, 1(1):1-6.
Hayden et al. (Jun. 15, 2011) "The Role of Matrix Metalloproteinases in Intestinal Epithelial Wound Healing During Normal and Inflammatory States", Journal of Surgical Research, 168(2):315-324.
Holte et al. (Jun. 2009) "Cyclo-oxygenase 2 Inhibitors and the Risk of Anastomotic Leakage After Fast-Track Colonic Surgery", British Journal of Surgery, 96(6):650-654.
Kaemmer et al. (Oct. 2010) "Erythropoietin (EPO) Influences Colonic Anastomotic Healing in a Rat Model by Modulating Collagen Metabolism", Journal of Surgical Research, 163(2):e67-e72.
Kiyama et al. (Sep. 2002) "Tacrolimus Enhances Colon Anastomotic Healing in Rats", Wound Repair and Regeneration, 10(5):308-313.
Klein et al. (Jan. 2011) "Effect of Diclofenac on Cyclooxygenase-2 Levels and Early Breaking Strength of Experimental Colonic Anastomoses and Skin Incisions", European Surgical Research, 46(1):26-31.
Klein et al. (Jul. 18, 2010) "Physiology and Pathophysiology of Matrix Metalloproteases", Amino Acids, 41(2): 271-290.
Krarup et al. (Apr. 26, 2013) "Expression and Inhibition of Matrix Metalloproteinase (MMP)-8, MMP-9 and MMP-12 in Early Colonic Anastomotic Repair", International Journal of Colorectal Disease, 28(8):1151-1159.
Martens et al. (Dec. 1991) "Postoperative changes in collagen synthesis in intestinal anastomoses of the rat: differences between small and large bowel", Gut, 32(12):1482-1487.
Moran et al. (May 15, 2007) "The Effect of Erythropoietin on Healing of Obstructive vs Nonobstructive Left Colonic Anastomosis: An Experimental Study", World Journal of Emergency Surgery, 2:13(6 pages).
Munireddy et al. (Dec. 2010) "Intra-abdominal Healing: Gastrointestinal Tract and Adhesions", Surgical Clinics of North America, 90(6):1227-1236(10 pages).
Øines et al. (Sep. 21, 2014) "Pharmacological Interventions for Improved Colonic Anastomotic Healing: A Meta-Analysis", World Journal of Gastroenterology, 20(35):12637-12648.
Raptis et al. (Mar. 2012) "The Effects of Tacrolimus on Colonic Anastomotic Healing in Rats", International Journal of Colorectal Disease, 27(3):299-308.
Savage et al. (Aug. 1997) "Role of Matrix Metalloproteinases in Healing of Colonic Anastomosis", Diseases of the Colon & Rectum, 40(8):962-970.
Siemonsma et al. (Mar. 1, 2003) "Doxycycline Improves Wound Strength After Intestinal Anastomosis in the Rat", Surgery, 133(3):268-276.
Thompson et al. (2006) "Clinical Review: Healing in Gastrointestinal Anastomoses, Part I", Microsurgery, 26(3):131-136.
Vandenbroucke et al. (Dec. 2014) "Is There New Hope for Therapeutic Matrix Metalloproteinase Inhibition?", Nature Reviews Drug Discovery, 13(12):904-927.
Witte et al. (Aug. 2003) "Repair of Full-thickness Bowel Injury", Critical Care Medicine, 31(8 Suppl):S538-S546.
International Search Report And Written Opinion For Patent Application No. PCT/IB2022/052795, dated Oct. 10, 2022, 17 pages.
International Search Report and Written Opinion received for Application No. PCT/IB2022/052796, dated Oct. 11, 2022, 18 pages.
International Search Report and Written Opinion received for Application No. PCT/IB2022/052822, dated Oct. 13, 2022, 18 pages.
International Search Report and Written Opinion received for PCT Application No. PCT/IB2022/052798, dated Aug. 18, 2022, 14 pages.

(56) References Cited

OTHER PUBLICATIONS

International Search Report and Written Opinion received for PCT Application No. PCT/IB2022/052804, dated Jul. 8, 2022, 16 pages.
International Search Report and Written Opinion received for PCT Application No. PCT/IB2022/052806, dated Jul. 27, 2022, 17 pages.
International Search Report and Written Opinion received for PCT Application No. PCT/IB2022/052807, dated Jul. 7, 2022, 14 pages.
International Search Report and Written Opinion received for PCT Application No. PCT/IB2022/052809, dated Jul. 27, 2022, 17 pages.
International Search Report and Written Opinion received for PCT Application No. PCT/IB2022/052811, dated Jul. 7, 2022, 18 pages.
International Search Report and Written Opinion received for PCT Application No. PCT/IB2022/052813, dated Jul. 27, 2022, 15 pages.
International Search Report and Written Opinion received for PCT Application No. PCT/IB2022/052815, dated Jul. 20, 2022, 13 pages.
International Search Report and Written Opinion received for PCT Application No. PCT/IB2022/052816, dated Jul. 12, 2022, 16 pages.
International Search Report and Written Opinion received for PCT Application No. PCT/IB2022/052818, dated Aug. 10, 2022, 14 pages.
Invitation to Pay Additional Fees received for PCT Application No. PCT/IB2022/052795, dated Jul. 20, 2022, 11 pages.
Invitation to Pay Additional Fees received for PCT Application No. PCT/IB2022/052796, dated Jul. 27, 2022, 13 pages.
Invitation to Pay Additional Fees received for PCT Application No. PCT/IB2022/052822, dated Aug. 12, 2022, 13 pages.
(Mar. 24, 2022) What are Stents?, NIH National Heart, Lung, and Blood Institute, 3 pages.
Maurus et al. (2004) "Bioabsorbable Implant Material Review", Operative Techniques in Sports Medicine, 12:158-160.

\* cited by examiner

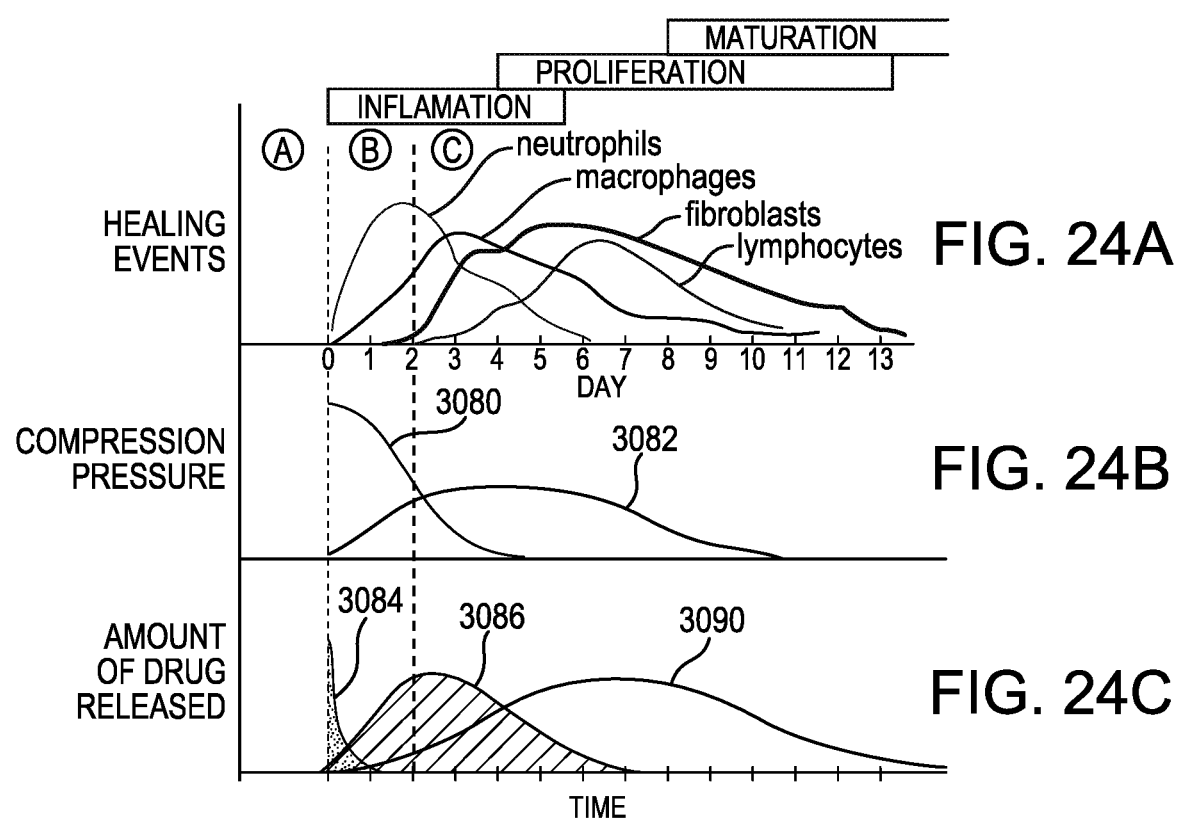

COMPRESSIBLE ADJUNCTS WITH HEALING-DEPENDENT DEGRADATION PROFILE

FIELD OF THE INVENTION

The present disclosure relates generally to compressible adjuncts and methods of using compressible adjuncts.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling.

Various implantable materials have been developed for use in combination with stapling tissue, however there remains a need for improved materials that address some of the aforementioned problems.

SUMMARY

In general, compressible adjuncts and methods for repairing tissue are provided. In one embodiment, a compressible adjunct kit for use with a staple cartridge is provided and includes a biocompatible adjunct material and a pretreatment fluid. The biocompatible adjunct material is configured to be releasably retained on a staple cartridge and is configured to be delivered to tissue by deployment of staples in the staple cartridge. The adjunct material can be in the form of a porous polymer body. The pretreatment fluid is configured to be applied to the adjunct material to change the adjunct material from an untreated state to a treated state. The adjunct material in the untreated state is configured to exhibit a first degradation profile when delivered to tissue. The adjunct material in the treated state is configured to exhibit a second degradation profile, different from the first degradation profile, when delivered to tissue.

The pretreatment fluid can have a variety of configurations. In one embodiment, the pretreatment fluid can be configured to increase a rate of degradation of the second degradation profile with respect to the first degradation profile. In another embodiment, the pretreatment fluid can be configured to cause the adjunct in the treated state to increase a pH adjacent to the adjunct when delivered to tissue. In other aspects, the pretreatment fluid can be configured to increase a degree of hydrophilicity of the adjunct in the treated state. In another embodiment, the pretreatment fluid can be configured to decrease a rate of degradation of the second degradation profile with respect to the first degradation profile. In another embodiment, the pretreatment fluid can be configured to form a coating that is deposited on at least a portion of the adjunct in the treated state. In yet another embodiment, the pretreatment fluid can be configured to react with the adjunct material to change a terminal functional group of at least a portion of a polymer chain forming the porous polymer body in the treated state. In other aspects, the pretreatment fluid can be configured to increase a degree of hydrophobicity of the adjunct in the treated state as compared to the untreated state. In yet another embodiment, the pretreatment fluid can be configured to form a sealant that seals at least a portion of pores in the porous polymer body. In other aspects, the pretreatment can be configured to terminate at least a portion of a plurality of polymer chains of the porous polymer body such that an average length of the plurality of polymer chains of the polymer body in the treated state is less than an average length of the plurality of polymer chains of the polymer body in the untreated state.

In another embodiment, a surgical method is provided and includes treating an untreated biocompatible adjunct material including a porous polymer body to produce a treated adjunct material having an altered degradation profile with respect to the untreated adjunct material. The method also includes releasably retaining the treated adjunct material on a staple cartridge, and actuating a surgical stapling device having the staple cartridge and treated adjunct material thereon to staple the treated adjunct material to tissue.

In one embodiment, treating the biocompatible adjunct material includes immersing the adjunct material within a pretreatment fluid. The altered degradation profile can have a rate of degradation that is greater than a degradation profile of the untreated adjunct material. In other embodiments, treating the adjunct material causes the adjunct material to increase a pH adjacent to the treated adjunct material when delivered to tissue. In another embodiment, treating the adjunct material increases a degree of hydrophilicity of the treated adjunct material as compared to an untreated adjunct material. In another embodiment, the altered degradation profile has a rate of degradation that is less than a degradation profile of the untreated adjunct material.

In another embodiment, treating the adjunct material applies a coating to at least a portion of the adjunct material. In another embodiment, treating the adjunct material includes apply a pretreatment fluid that reacts with the porous polymer body of the adjunct material and changes a terminal functional group of polymer chains forming the polymer body. In another embodiment, treating the adjunct material increases a degree of hydrophobicity of the treated adjunct material as compared to an untreated adjunct material. In another embodiment, treating the adjunct material includes apply a pretreatment fluid that forms a sealant that seals at least a portion of pores of the porous body.

In another embodiment, treating the adjunct material includes apply a pretreatment fluid that terminates at least a portion of the polymer chains of the polymer body such that an average length of polymer chains of the polymer body of the treated adjunct material is less than an average length of polymer chains of the polymer body of the untreated adjunct material. A rate of degradation of the second degradation profile is increased with respect to the first degradation profile.

In another embodiment, a compressible adjunct for use with a staple cartridge is provided and includes a biocompatible adjunct material configured to be releasably retained on a staple cartridge and configured to be delivered to tissue by deployment of staples in the staple cartridge. The adjunct material is formed from a porous polymer body and is configured to exhibit a first stiffness in compression that is approximately constant during a first time period from contact with the tissue. The adjunct material is further configured to exhibit a second stiffness in compression during a second time period following the first time period. The second stiffness is less than the first stiffness and is configured to decrease with time as a function of at least one of oxidation, enzyme-catalyzed hydrolysis, and change of pH resulting from interaction with at least one physiological element released from the tissue during healing progression of the tissue.

In one embodiment, the adjunct is configured to adopt the second stiffness in response to oxidation resulting from reaction with the physiological element comprising a reactive oxygen species. In another embodiment, the adjunct is configured to oxidize in response to reaction with a reactive oxygen species released by a mature blood cell or a fybrocyte. The reactive oxygen species can include a superoxide. In another embodiment, the adjunct is configured to oxidize in response to reaction with a reactive oxygen species released by an inflammatory cell. The inflammatory cell can be at least one of a leukocyte, a neutrophil, a basophil, an eosinophil, a lymphocyte, a monocytes, and a macrophage. In another embodiment, the reactive oxygen species is at least one of an oxygen containing enzyme, a free radical, a superoxide, and a peroxide. In another embodiment, the reactive oxygen species is at least one of $O^{2-}$, $H_2O_2$, $NO$, and $HOCl$.

In another embodiment, the adjunct is configured adopt the second stiffness in response to hydrolysis catalyzed by an enzyme. The enzyme can be a lysozyme. In another embodiment, the adjunct is configured to adopt the second stiffness in response to a decrease in pH resulting from the presence of the at least one physiological element.

In other aspects, a stapling assembly is provided and includes a staple cartridge, an anvil, and an adjunct. The staple cartridge has a plurality of staples disposed therein that are arranged in staple rows and configured to be deployed into tissue. The staple cartridge also includes a knife slot extending therethrough between the staple rows for receiving a knife to cut tissue along a cut line. The anvil is positioned opposite the staple cartridge. The adjunct is configured to be releasably retained on the staple cartridge or the anvil. The adjunct can be in the form of a biocompatible porous polymer material configured to be delivered to tissue by deployment of the plurality of staples from the staple cartridge. The adjunct can have a first shape, and at least one first portion of the adjunct can be configured to exhibit a first expansion behavior in response to receipt of a unit volume of fluid, and at least one second portion of the adjunct can be configured to exhibit a second expansion behavior, different from the first expansion behavior, in response to receipt of the unit volume of fluid such that the adjunct adopts a second shape that is different from the first shape. The difference between the first and second expansion behavior can be configured to apply different pressures to different portions of tissue having the adjunct stapled thereto.

In one embodiment, an amount of expansion of the adjunct is configured to provide hemostasis at the cut line. In another embodiment, an amount of expansion of the adjunct is configured to seals holes created in the issue by the plurality of staples when the staples are ejected into tissue.

In another embodiment, the at least one second portion of the adjunct is positioned adjacent to the knife slot and the at least one first portion of the adjunct is spaced a distance from the knife slot, and the second shape can be configured to apply a greater pressure than the first shape.

In another embodiment, the at least one second portion includes a swellable material that differs from the biocompatible porous polymer material. The swellable material can include a hydrogel. In another embodiment, the swellable material includes a porous, solid material, and the swellable material is housed in a compressed state within a fluid-soluble capsule. The capsule can be configured to release the swellable material after a predetermined time period from contact with the fluid.

In another embodiment, a rate of expansion of the at least one second portion of the adjunct in response to receipt of the unit volume of fluid is greater than a rate of expansion of the at least one first portion of the adjunct in response to receipt of the unit volume of fluid.

In another embodiment, at least one staple of the plurality of staples includes at least one leg including a plurality of barbs. When the plurality of staples are ejected into the adjunct and tissue, the plurality of barbs are configured to permit expansion of adjunct in a first direction and inhibit retraction of the adjunct in a second direction, opposite the first direction.

In another embodiment, the at least one second portion includes a film overlying a surface of the adjunct.

In another embodiment, the adjunct further includes a color transition dye that changes color during expansion of the adjunct. The color transition dye can be a hydrochromic ink configured to change color in response to contact with at least one of a fluid and lipids.

In another embodiment, an adjunct for use with a staple cartridge is provided. The adjunct includes a biocompatible adjunct configured to be releasably retained on a staple cartridge body and configured to be delivered to tissue by deployment of staples in the cartridge body. The adjunct is formed as a porous body including a first polymer and a second polymer. The first polymer is configured to degrade according to a first degradation profile as a function of at least one of hydrolysis in response to interaction with water and heating to a physiological temperature. The second polymer is configured to degrade according to a second degradation profile as a function of at least one of oxidation, enzyme-catalyzed hydrolysis, and change of pH resulting from interaction with at least one physiological element released from the tissue during healing progression of the tissue.

In one aspect, the first polymer is configured to expand in response to absorption of water and to exert a first compressive pressure on the tissue having a magnitude that is dependent upon the first degradation profile, the second polymer is configured to expand in response to degradation of the first polymer and to exert a second compressive pressure on the tissue having a magnitude that is dependent upon the first and second degradation profiles, and a maximum magnitude of the second compressive pressure is less than a maximum magnitude of the first compressive pressure.

In another embodiment, the first polymer is configured to inhibit interaction of the second polymer with at least a portion of the at least one physiological element. The first polymer can overlay the second polymer.

In another embodiment, a degradation rate of the first polymer according to the first degradation profile is greater than a degradation rate of the second polymer according to the second degradation profile.

In another embodiment, the first polymer is a moisture absorbing powder or foam.

In another embodiment, the at least one physiological element includes a reactive oxygen species. The reactive oxygen species can include at least one of an oxygen containing enzyme, a free radical, a superoxide, and a peroxide.

In another embodiment, the adjunct includes a first drug retained by the first polymer and configured for release during degradation of the first polymer. The first drug can include a hemostatic drug. The adjunct can further include a second drug retained by the second polymer and configured for release during degradation of the second polymer. The second drug can be configured to promote tissue remodeling. In another embodiment, the second drug is configured for at least one of bolus release and gradual release based upon a geometry of the second polymer.

In an embodiment, a method for treating tissue is provided. The method includes securing, by one or more staples, a porous biocompatible adjunct to tissue. The adjunct can include a first polymer and a second polymer. The adjunct receives at least one of water and heat sufficient to raise a temperature of the adjunct to a physiological temperature, thereby causing the first polymer to degrade according to a first degradation profile. The adjunct receives at least one physiological element released from the tissue during healing progression of the tissue, thereby causing the second polymer to degrade according to a second degradation profile as a function of at least one of oxidation, enzyme-catalyzed hydrolysis, and change of pH resulting from interaction with the at least one physiological element.

In one embodiment, the first polymer expands in response to receipt of the water to exert a first compressive pressure on the tissue having a magnitude that is dependent upon the first degradation profile, and the second polymer expands in response to degradation of the first polymer and exerts a second compressive pressure on the tissue having a magnitude that is dependent at least upon the first and second degradation profiles. A maximum magnitude of the second compressive pressure is less than a maximum magnitude of the first compressive pressure.

In another embodiment, the second compressive pressure is dependent upon the first degradation profile and the second degradation profile.

In another embodiment, the first polymer inhibits interaction of the second polymer with at least a portion of the at least one physiological element. The at least one physiological element can include a reactive oxygen species.

In another embodiment, the first polymer overlies the second polymer. In another embodiment, the first polymer is at least one of moisture absorbing powder and a foam.

In another embodiment, a degradation rate of the first polymer according to the first degradation profile is greater than a degradation rate of the second polymer according to the second degradation profile.

In another embodiment, the adjunct further includes a first drug retained by the first polymer that is released during degradation of the first polymer. The first drug can be a hemostatic drug.

In another embodiment, the adjunct further includes a second drug retained by the second polymer that is released during degradation of the second polymer. The second drug can promote tissue remodeling.

In another embodiment, the method further includes at least one of a bolus release and a gradual release of the second drug based upon a geometry of the second polymer.

BRIEF DESCRIPTION OF THE DRAWINGS

This invention will be more fully understood from the following detailed description taken in conjunction with the accompanying drawings, in which:

FIG. 24A is a plot illustrating healing events within the tissue coupled to the composite adjunct as a function of time;

FIG. 24B is a plot illustrating compressive pressure applied by the first and second polymers of the composite adjunct of FIG. 19 to the tissue, respectively, as a function of time; and FIG. 24C is a plot illustrating release rates of first and second drugs retained by the first and second polymers of the composite adjunct of FIG. 19, respectively, as a function of time.

DETAILED DESCRIPTION

Figure 1:
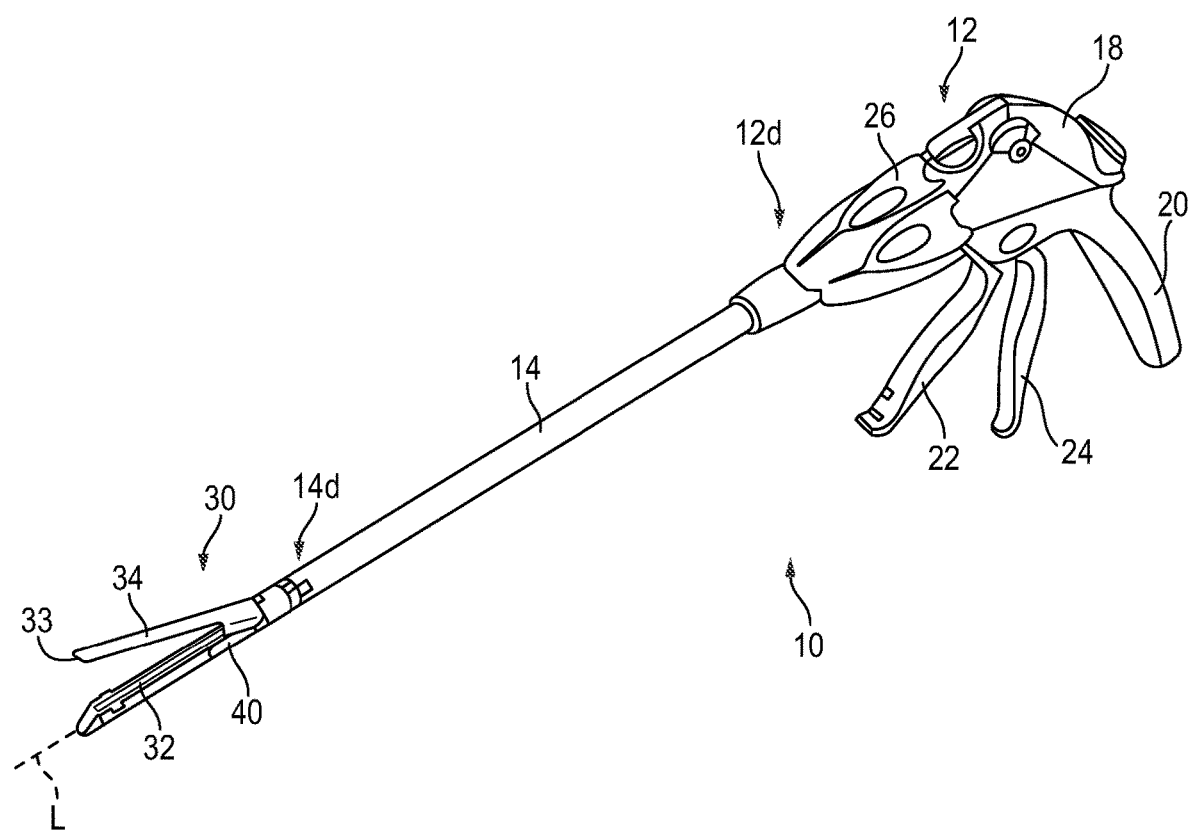
FIG. 1 is a perspective view of one exemplary embodiment of a conventional surgical stapling and severing instrument.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

It can be desirable to use one or more biologic materials and/or synthetic materials, referred to herein as "adjuncts," in conjunction with surgical instruments to help improve surgical procedures. "Adjuncts" are also referred to herein as "adjunct materials." While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing, and/or is experiencing another tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissue's movement around these puncture sites can minimize the size the holes may grow to under tension. In some instances, the adjunct(s) can be configured to wick or absorb beneficial fluids, e.g., sealants, blood, glues, and the like, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts.

In other embodiments, the adjunct(s) can be used with surgical instruments that are configured to seal tissue without using staples (e.g., by using energy, such as RF or ultrasound), for example, as described in U.S. Pat. No. 10,172,611, which is incorporated by reference herein in its entirety.

In some instances, the adjunct(s) can be configured to compensate for variations in tissue thickness when the adjunct(s) are stapled to tissue. In such instances, the adjunct can be also be referred to as a "tissue thickness compensator." A tissue thickness compensator has an uncompressed (un-deformed), or pre-deployed, height that is greater than the height of a staple that is in a formed configuration. Additional details on exemplary tissue thickness compensators can be found in, for example, U.S. Pat. No. 8,864,007, which is incorporated by reference herein in its entirety. A tissue thickness compensator can be attached and released from a staple cartridge in a variety of ways, for example, as described in U.S. Pat. Nos. 9,272,406, and 10,136,890, each of which is incorporated by reference herein in its entirety.

In addition to the disclosures herein, additional details pertaining to the adjunct(s) and other exemplary adjuncts can be found in, for example, U.S. Pat. Nos. 10,172,611 and 10,433,846 and U.S. patent application Ser. No. 17/009,769, filed on Sep. 1, 2020, and entitled "Compressible Non-Fibrous Adjuncts," each of which is incorporated herein by reference in its entirety.

Alternatively or in addition, the adjunct(s) can be configured to promote tissue ingrowth. In various instances, it is desirable to promote the ingrowth of tissue into an implantable adjunct, to promote the healing of the treated tissue (e.g., stapled and/or incised tissue), and/or to accelerate the patient's recovery. More specifically, the ingrowth of tissue into an implantable adjunct may reduce the incidence, extent, and/or duration of inflammation at the surgical site. Tissue ingrowth into and/or around the implantable adjunct may, for example, manage the spread of infections at the surgical site. The ingrowth of blood vessels, especially white blood cells, for example, into and/or around the implantable adjunct may fight infections in and/or around the implantable adjunct and the adjacent tissue. Tissue ingrowth may also encourage the acceptance of foreign matter (e.g., the implantable adjunct and the staples) by the patient's body and may reduce the likelihood of the patient's body rejecting the foreign matter. Rejection of foreign matter may cause infection and/or inflammation at the surgical site.

Alternatively or in addition, the adjunct(s) can have medicant(s) thereon and/or therein. The medicant(s) can vary depending on the desired effect of the medicant(s) on the surrounding tissue. As a non-limiting example, medicant(s) can be provided to influence hemostasis, inflammation, macrophages, and/or fibroblasts. Medicant(s) can be mixed or combined in any combination or a medicant can be provided alone, again depending on the desired effect on the tissue. The medicant(s) can be eluted from the adjunct(s) in a variety of different ways. As non-limiting examples, coatings on the adjunct(s) can be varied to be absorbed at different times, thereby releasing the medicant(s) at different times; the adjunct(s) can be varied to allow diffusion of the medicant(s) across the adjunct(s) at varying rates; the adjunct(s) can vary in molecular weight and/or physical characteristics to cause release of the medicant(s) at different times; etc. In addition to the disclosures herein, additional details on drug eluting adjuncts can be found in U.S. Pat. Nos. 9,232,941 and 10,569,071, each of which is incorporated herein by reference in its entirety.

Surgical Stapling Instruments

A variety of surgical instruments can be used in conjunction with the adjunct(s) and/or medicant(s) disclosed herein. The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12*d* of the handle assembly 12, and an end effector 30 at a distal end 14*d* of the shaft 14. The end effector 30 has opposed lower and upper jaws 32, 34, although other types of end effectors can be used with the shaft 14, handle assembly 12, and components associated with the same. The lower jaw 32 has a staple channel 56 configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 or other cutting element can be associated with the firing system to cut tissue during the stapling procedure.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent a distal end 12*d* thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

Figure 2:
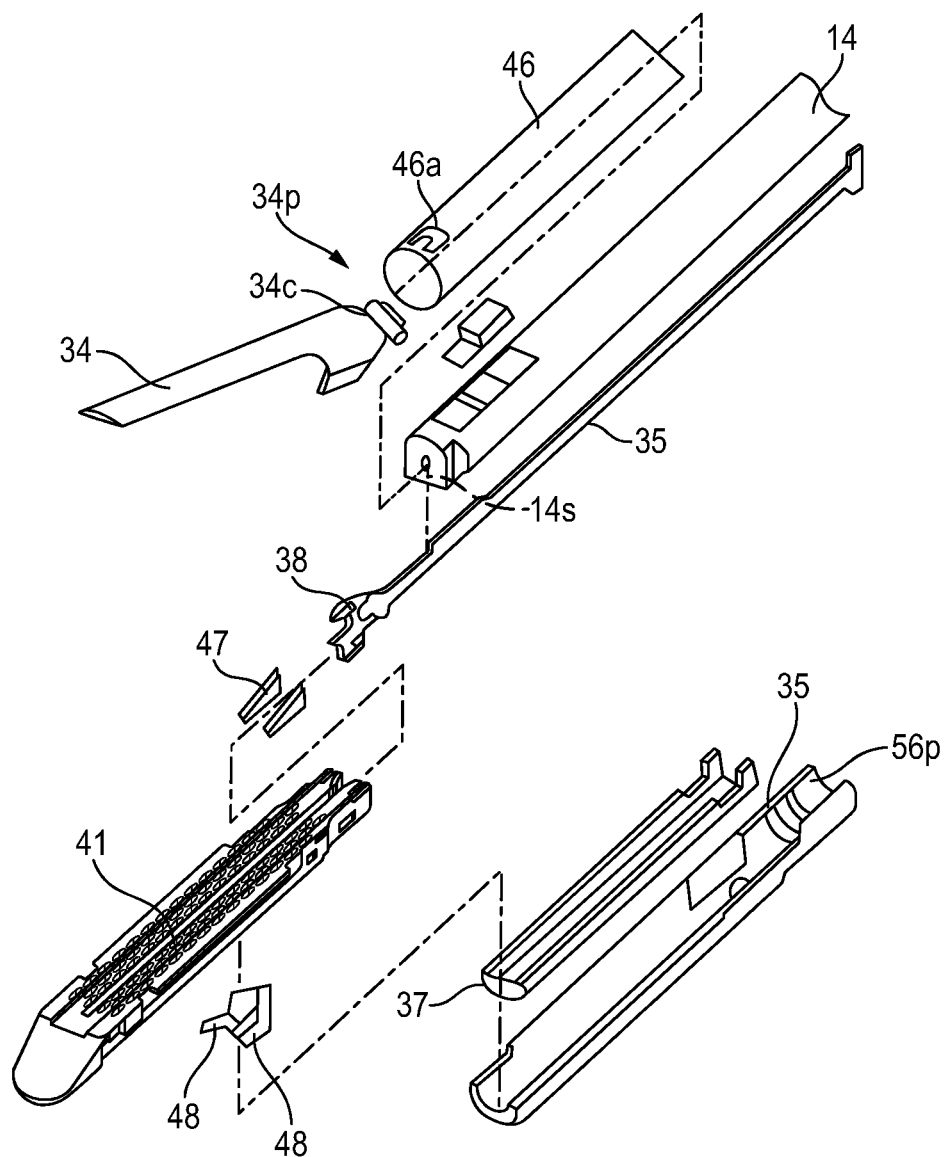
FIG. 2 is a top view of a staple cartridge for use with the surgical stapling and severing instrument of FIG. 1.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
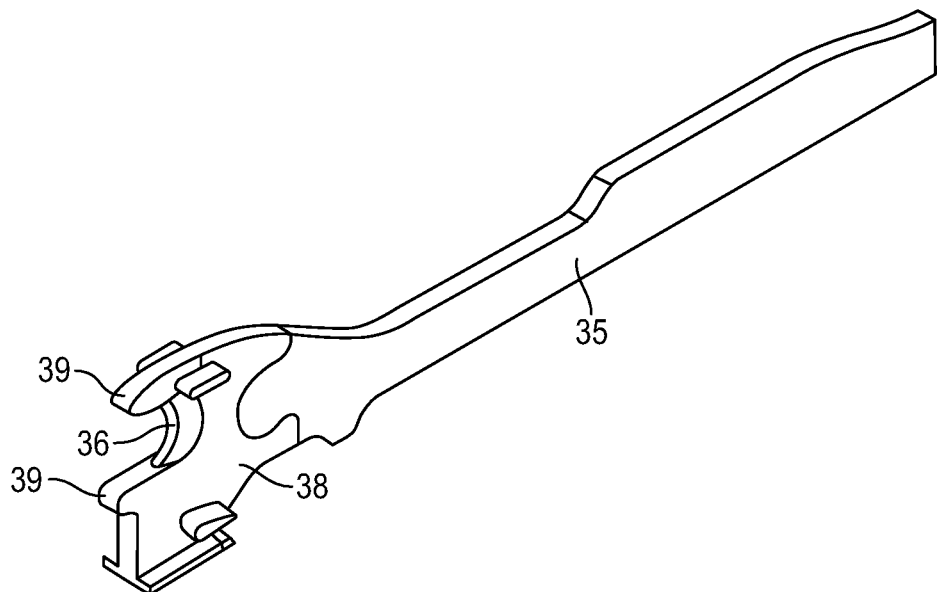
FIG. 3 is a perspective view of a firing bar of the surgical stapler of FIG. 1, the firing bar having an E-beam at a distal end thereof.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47 shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
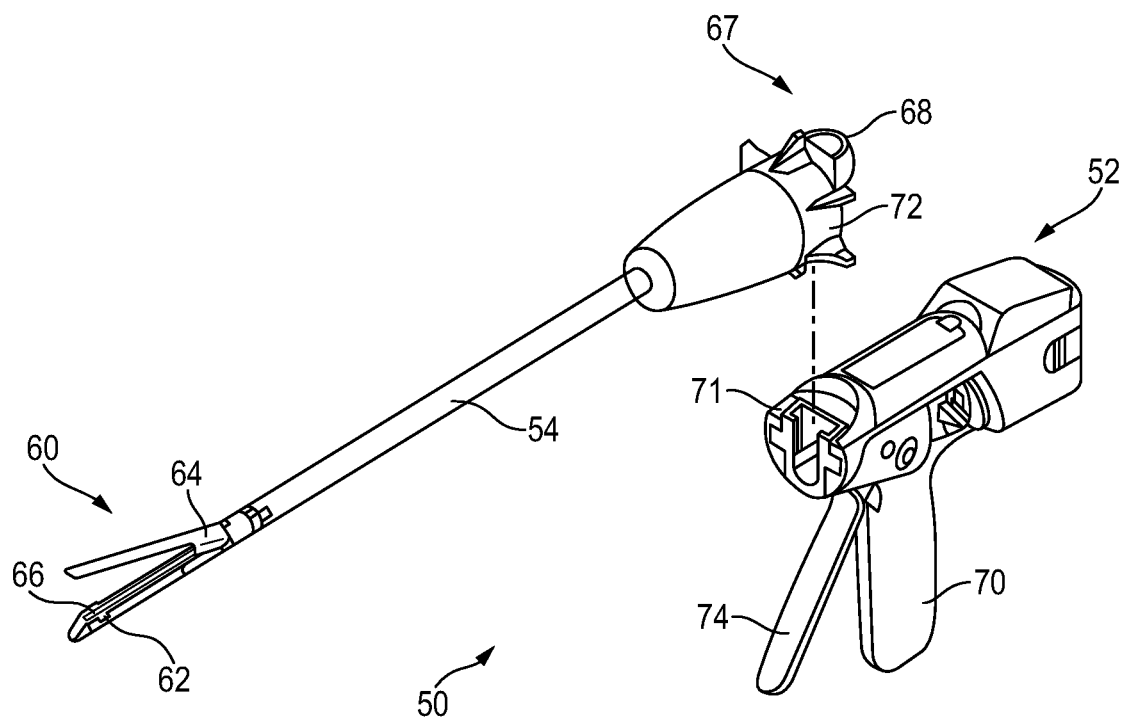
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
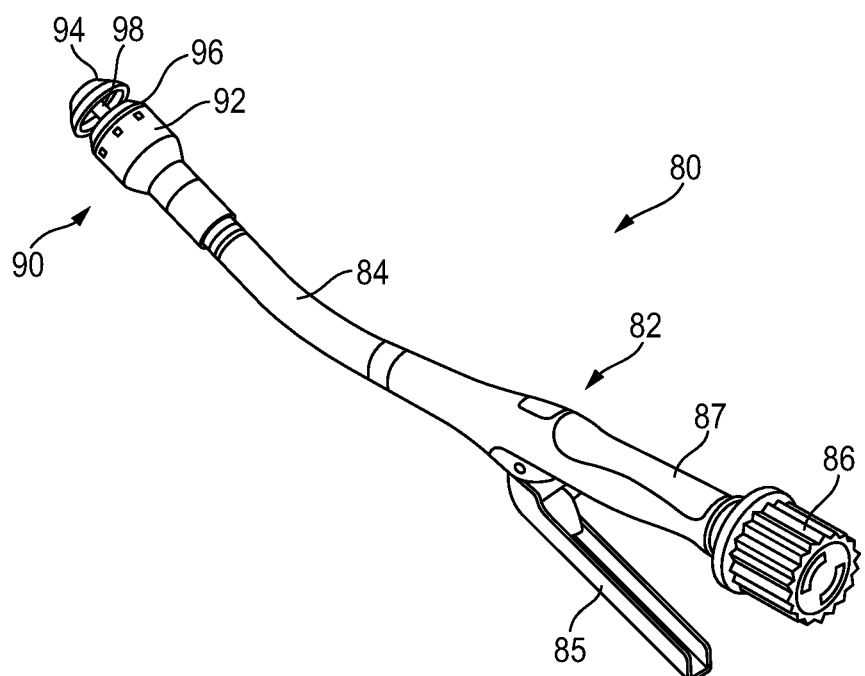
FIG. 5 is a perspective view of yet another embodiment of a surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft can be disposed within the cartridge assembly 92 and extend distally outside of the cartridge assembly 92, terminating in a distal mating feature. The second portion of the shaft can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, e.g., move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, and 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, and U.S. patent application Ser. No. 14/300,954, entitled "Adjunct Materials and Methods of Using Same in Surgical Methods for Tissue Sealing," and filed on Jun. 10, 2014, which are hereby incorporated by reference herein in their entireties.

Implantable Adjuncts

Figure 6:
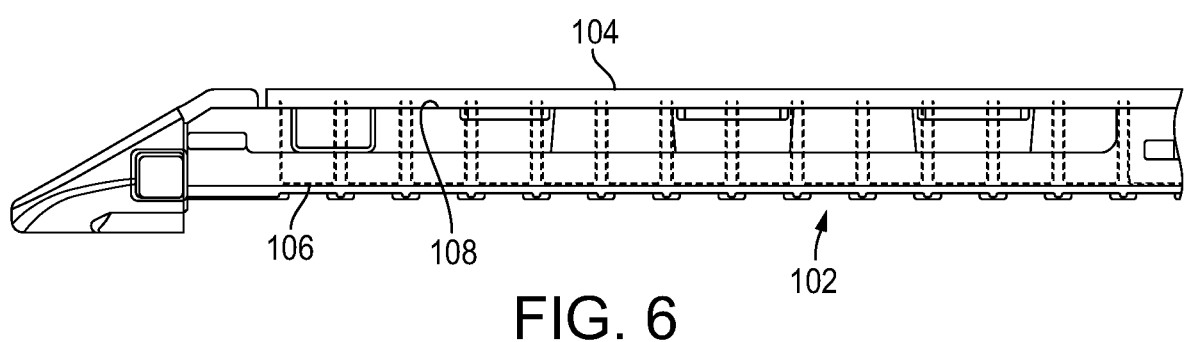
FIG. 6 is a longitudinal cross-sectional view of an exemplary embodiment of a staple cartridge having an exemplary adjunct attached to a top or deck surface thereof.

As indicated above, various implantable adjuncts are provided for use in conjunction with surgical stapling instruments. When used in conjunction with a surgical stapler, the adjunct(s) can be disposed between and/or on jaws of the stapler, incorporated into a staple cartridge disposed in the jaws, or otherwise placed in proximity to the staples. For example, as shown in FIG. 6, an adjunct 104 is positioned against a staple cartridge 102. For sake of simplicity, the adjunct 104 is generally illustrated in FIG. 6, and various structural configurations of the adjunct are described in more detail below. While partially obstructed in FIG. 6, the staple cartridge 102 includes staples 106 that are configured to be deployed into tissue. The staples 106 can have any suitable unformed (pre-deployed) height. For example, the staples 106 can have an unformed height between about 2 mm and 4.8 mm. Prior to deployment, the crowns of the staples can be supported by staple drivers (not shown).

In the illustrated embodiment, the adjunct 104 can be releasably mated to at least a portion of the top surface or deck surface 108 of the staple cartridge 102. In some embodiments, the top surface 108 of the staple cartridge 102 can include one or more surface features. Alternatively, or in addition, one or more adhesives can be used to releasably mate the adjunct to the staple cartridge 102. The one or more surface features and/or the one or more adhesives can be configured to engage the adjunct 104 to avoid undesirable movements of the adjunct 104 relative to the staple cartridge 102 and/or to prevent premature release of the adjunct 104 from the staple cartridge 102. Exemplary surface features are described in U.S. Patent Publication No. 2016/0106427, which is incorporated by reference herein in its entirety. Additional details on adhesives for temporary attachment to instruments and other exemplary adhesives can be found in U.S. Pat. Nos. 9,282,962, 10,172,617, 10,172,618, 10,258,332, 10,517,592, 10,548,593, 10,568,621, and 10,588,623, each of which is incorporated by reference herein in its entirety. Additional details on attachment methods and other exemplary methods can be found in U.S. Pat. Nos. 10,166,023 and 10,349,939 and U.S. patent application Ser. No. 17/022,520, filed on Sep. 16, 2020, and entitled "Method of Applying Buttress to End Effector of Surgical Stapler," each of which is incorporated by reference herein in its entirety.

Figure 7:
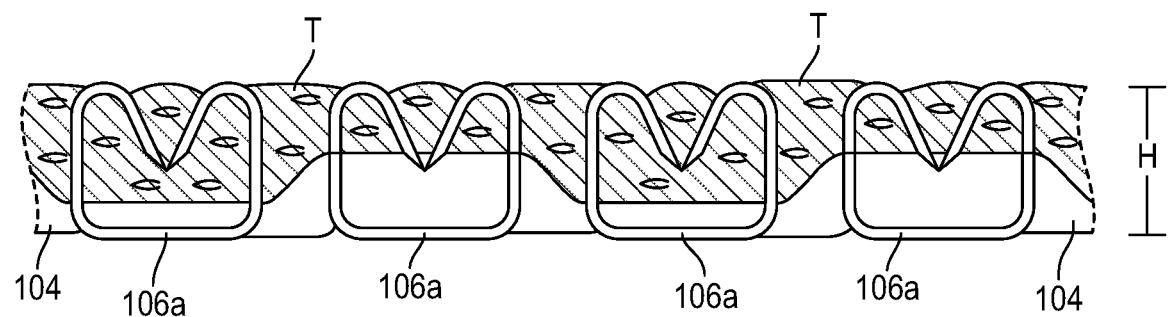
FIG. 7 is a partial-schematic illustrating the adjunct of FIG. 6 in a tissue deployed condition.

In certain instances, the adjunct can be compressible to permit the adjunct to compress to varying heights to thereby compensate for different tissue thickness that are captured within a deployed staple. For example, as illustrated in FIG. 6, the adjunct 104 has an uncompressed (un-deformed), or pre-deployed, height and is configured to deform to one of a plurality of compressed (deformed), or deployed, heights. As such, the adjunct 104 can have an uncompressed height which is greater than the fired height of the staples 106 disposed within the staple cartridge 102 (e.g., the height (H) of the fired staple 106a in FIG. 7). That is, the adjunct 104 can have an un-deformed state in which a maximum height of the adjunct 104 is greater than a maximum height of a fired staple (e.g., a staple that is in a formed configuration). In such instances, the adjunct can be referred to as a "tissue thickness compensator." In one embodiment, the uncompressed height of the adjunct 104 can be about 10% taller, about 20% taller, about 30% taller, about 40% taller, about 50% taller, about 60% taller, about 70% taller, about 80% taller, about 90% taller, or about 100% taller than the fired height of the staples 106. In certain embodiments, the uncompressed height of the adjunct 104 can be over 100% taller than the fired height of the staples 106, for example.

The adjuncts can have a variety of configurations, and can be formed from various materials. In general, an adjunct can be formed from one or more of a film, a foam, an injection molded thermoplastic, a vacuum thermoformed material, a fibrous structure, an additive manufacturing material, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Examples of various foam adjuncts are further described in previously mentioned U.S. Pat. No. 8,393,514 entitled "Selectively Orientable Implantable Fastener Cartridge" and filed Sep. 30, 2010, which is incorporated by reference herein in its entirety.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways, for example, it can be an extruded or a compression molded film.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

In other embodiments, the adjunct can be formed using a 3D printing process(es) compatible with absorbable polymers. Non-limiting examples of suitable 3D printing processes include stereolithography (SLA or SL), material jetting, selective laser sintering (SLS), and fused filament fabrication as understood by a person skilled in the art.

The adjunct can also be a hybrid construct, such as a laminate composite or melt-locked interconnected fiber. Examples of various hybrid construct adjuncts are further described in U.S. Pat. Pub. No. 2013/0146643 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

Materials

The adjuncts in accordance with the described techniques can be formed from various materials. The materials can be used in various embodiments for different purposes. The materials can be selected in accordance with a desired therapy to be delivered to tissue so as to facilitate tissue in-growth. The materials described below can be used to form an adjunct in any desired combination.

The materials can include bioabsorbable and biocompatible polymers, including homopolymers and copolymers. Non-limiting examples of homopolymers and copolymers include p-dioxanone (PDO or PDS), polyglycolic acid (PGA) (e.g., Dexon and Neoveil), poly(lactic-co-glycolic acid) (PLGA), polycaprolactone (PCL), polyglycolide (PGL), trimethylene carbonate (TMC), polylactic acid (PLA) (e.g., Linvatec Bioscrew and Bionx Implants Smart Screw), poly(trimethylene carbonate (PTMC), polyethylene diglycolate (PEDG), poly(propylene fumarate) (PPF), polyethylene ether (PEE), poly(ethylene glycol) (PEG), poly(N- isopropylacrylamide, poly(amino acid), poly(epoxycarbonate), poly(2-oxypropylene carbonate), poly(diol citrates), polymethacrylate anhydrides, poly(ethoxyethylene diglycolate), poly(glycolic acid-co-lactic acid) (PLA/PGA) (e.g., PLA/PGA materials used in Vicryl, Vicryl Rapide, Poly-Sorb, and Biofix), polyurethanes (such as Elastane, Biospan, Tecoflex, Bionate, and Pellethane fibers), polyorthoesters, polyanhydrides (e.g., Gliadel and Biodel polymers), polyoxaesters, polyesteramides (e.g., REVA ReZolve Stents), and tyrosine-based polyesteramides (e.g., TYRX). The copolymers can also include poly(lactic acid-co-polycaprolactone) (PLA/PCL) (e.g., 16-18 month hydrolyzed), poly(L-lactic acid-co-polycaprolactone) (PLLA/PCL), poly(glycolic acid-co-trimethylene carbonate) (PGA/TMC) (e.g., Maxon), Poly(glycolic acid-co-caprolactone) (PCL/PGA) (e.g., Monocryl and Capgly), PDS/PGA/TMC (e.g., Biosyn), PDS/PLA, PGA/PCL/TMC/PLA (e.g., Caprosyn), LPLA/DLPLA (e.g., Optima), PLGA-PCL (e.g., 15:85 (PCL: 50% D,L-Lactide: 50% Glycolide), 40:60 (PCL: 50% D,L-Lactide: 50% Glycolide), and 40:60 (PCL: 85% D,L-Lactide: 15% Glycolide), PLGA-PCL-PLGA, and PLGA-PEG-PLGA.

An adjunct can also include special polymer terminations, including (meth)acrylate and organically-derived polymers. Non-limiting examples of organically-derived polymers include those derived from collagen (e.g., Avitene, Endoavitene, Instat, Integran, Veritas, and Microfibrillar Collagen (MFC)).

An adjunct can also include active agents, such as active cell culture (e.g., diced autologous tissue, agents used for stem cell therapy (e.g., Biosutures and Cellerix S.L.), hemostatic agents, and tissue healing agents. Non-limiting examples of hemostatic agents can include cellulose such as oxidized Regenerated Cellulose (ORC) (e.g., Surgicel and Interceed), fibrin/thrombin (e.g., Thrombin-JMI, TachoSil, Tiseel, Floseal, Evicel, TachoComb, Vivostat, and Everest), autologous platelet plasma, gelatin (e.g., Gelfilm and Gelfoam), hyaluronic acid such as microfibers (e.g., yarns and textiles) or other structures based on hyaluronic acid, or hyaluronic acid-based hydrogels. The hemostatic agents can also include polymeric sealants such as, for example, bovine serum albumin and glutarldehyde, human serum albumin and polyethylene cross-linker, and ethylene glycol and trimethylene carbonate. The polymeric sealants can include FocalSeal surgical sealant developed by Focal Inc.

The adjuncts described herein can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response.

Non-limiting examples of antimicrobial agents include Ionic Silver, Aminoglycosides, Streptomycin, Polypeptides, Bacitracin, Triclosan, Tetracyclines, Doxycycline, Minocycline, Demeclocycline, Tetracycline, Oxytetracycline, Chloramphenicol, Nitrofurans, Furazolidone, Nitrofurantoin, Beta-lactams, Penicillins, Amoxicillin, Amoxicillin+Clavulanic Acid, Azlocillin, Flucloxacillin, Ticarcillin, Piperacillin+tazobactam, Tazocin, Biopiper TZ, Zosyn, Carbapenems, Imipenem, Meropenem, Ertapenem, Doripenem, Biapenem, Panipenem/betamipron, Quinolones, Ciprofloxacin, Enoxacin, Gatifloxacin, Gemifloxacin, Levofloxacin, Lomefloxacin, Moxifloxacin, Nalidixic Acid, Norfloxacin, Sulfonamides, Mafenide, Sulfacetamide, Sulfadiazine, Silver Sulfadiazine, Sulfadimethoxine, Sulfamethizole, Sulfamethoxazole, Sulfasalazine, Sulfisoxazole, Bactrim, Prontosil, Ansamycins, Geldanamycin, Herbimycin, Fidaxomicin, Glycopeptides, Teicoplanin, Vancomycin, Telavancin, Dalbavancin, Oritavancin, Lincosamides, Clindamycin, Lincomycin, Lipopeptide, Daptomycin, Macrolides, Azithromycin, Clarithromycin, Erythromycin, Roxithromycin, Telithromycin, Spiramycin, Oxazolidinones, Linezolid, Aminoglycosides, Amikacin, Gentamicin, Kanamycin, Neomycin, Netilmicin, Tobramycin, Paromycin, Paromomycin, Cephalosporins, Ceftobiprole, Ceftolozane, Cefclidine, Flomoxef, Monobactams, Aztreonam, Colistin, and Polymyxin B.

Non-limiting examples of antifungal agents include Triclosan, Polyenes, Amphotericin B, Candicidin, Filipin, Hamycin, Natamycin, Nystatin, Rimocidin, Azoles, Imidazole, Triazole, Thiazole, Allylamines, Amorolfin, Butenafine, Naftifine, Terbinafine, Echinocandins, Anidulafungin, Caspofungin, Micafungin, Ciclopirox, and Benzoic Acid.

Non-limiting examples of antiviral agents include uncoating inhibitors such as, for example, Amantadine, Rimantadine, Pleconaril; reverse transcriptase inhibitors such as, for example, Acyclovir, Lamivudine, Antisenses, Fomivirsen, Morpholinos, Ribozymes, Rifampicin; and virucidals such as, for example, Cyanovirin-N, Griffithsin, Scytovirin, α-Lauroyl-L-arginine ethyl ester (LAE), and Ionic Silver.

Non-limiting examples of anti-inflammatory agents include non-steroidal anti-inflammatory agents (e.g., Salicylates, Aspirin, Diflunisal, Propionic Acid Derivatives, Ibuprofen, Naproxen, Fenoprofen, and Loxoprofen), acetic acid derivatives (e.g., Tolmetin, Sulindac, and Diclofenac), enolic acid derivatives (e.g., Piroxicam, Meloxicam, Droxicam, and Lornoxicam), anthranilic acid derivatives (e.g., Mefenamic Acid, Meclofenamic Acid, and Flufenamic Acid), selective COX-2 inhibitors (e.g., Celecoxib (Celebrex), Parecoxib, Rofecoxib (Vioxx), Sulfonanilides, Nimesulide, and Clonixin), immune selective anti-inflammatory derivatives, corticosteroids (e.g., Dexamethasone), and iNOS inhibitors.

Non-limiting examples of growth factors include those that are cell signaling molecules that stimulate cell growth, healing, remodeling, proliferation, and differentiation. Exemplary growth factors can be short-ranged (paracrine), long ranged (endocrine), or self-stimulating (autocrine). Further examples of the growth factors include growth hormones (e.g., a recombinant growth factor, Nutropin, Humatrope, Genotropin, Norditropin, Saizen, Omnitrope, and a biosynthetic growth factor), Epidermal Growth Factor (EGF) (e.g., inhibitors, Gefitinib, Erlotinib, Afatinib, and Cetuximab), heparin-binding EGF like growth factors (e.g., Epiregulin, Betacellulin, Amphiregulin, and Epigen), Transforming Growth Factor alpha (TGF-a), Neuroregulin 1-4, Fibroblast Growth Factors (FGFs) (e.g., FGF1-2, FGF2, FGF11-14, FGF18, FGF15/19, FGF21, FGF23, FGF7 or Keratinocyte Growth Factor (KGF), FGF10 or KGF2, and Phenytoin), Insuline-like Growth Factors (IGFs) (e.g., IGF-1, IGF-2, and Platelet Derived Growth Factor (PDGF)), Vascular Endothelial Growth Factors (VEGFs) (e.g., inhibitors, Bevacizumab, Ranibizumab, VEGF-A, VEGF-B, VEGF-C, VEGF-D and Becaplermin).

Additional non-limiting examples of the growth factors include cytokines, such as Granulocyte Macrophage Colony Stimulating Factors (GM-CSFs) (e.g., inhibitors that inhibit inflammatory responses, and GM-CSF that has been manufactured using recombinant DNA technology and via recombinant yeast-derived sources), Granulocyte Colony Stimulating Factors (G-CSFs) (e.g., Filgrastim, Lenograstim, and Neupogen), Tissue Growth Factor Beta (TGF-B), Leptin, and interleukins (ILs) (e.g., IL-la, IL-lb, Canakinumab, IL-2, Aldesleukin, Interking, Denileukin Diftitox, IL-3, IL-6, IL-8, IL-10, IL-11, and Oprelvekin). The non-limiting examples of the growth factors further include erythropoietin (e.g., Darbepoetin, Epocept, Dynepo, Epomax, NeoRecormon, Silapo, and Retacrit).

Non-limiting examples of analgesics include Narcotics, Opioids, Morphine, Codeine, Oxycodone, Hydrocodone, Buprenorphine, Tramadol, Non-Narcotics, Paracetamol, acetaminophen, NSAIDS, and Flupirtine.

Non-limiting examples of anesthetics include local anesthetics (e.g., Lidocaine, Benzocaine, and Ropivacaine) and general anesthetic.

Non-limiting examples of tissue matrix degradation inhibitors that inhibit the action of metalloproteinases (MMPs) and other proteases include MMP inhibitors (e.g., exogenous MMP inhibitors, hydroxamate-based MMP inhibitors, Batimastat (BB-94), Ilomastat (GM6001), Marimastat (BB2516), Thiols, Periostat (Doxycycline), Squaric Acid, BB-1101, Hydroxyureas, Hydrazines, Endogenous, Carbamoylphosphates, Beta Lactams, and tissue Inhibitors of MMPs (TIMPs)).

Non-limiting examples of anti-cancer agents include monoclonial antibodies, bevacizumab (Avastin), cellular/chemoattractants, alkylating agents (e.g., Bifunctional, Cyclophosphamide, Mechlorethamine, Chlorambucil, Melphalan, Monofunctional, Nitrosoureas and Temozolomide), anthracyclines (e.g., Daunorubicin, Doxorubicin, Epirubicin, Idarubicin, Mitoxantrone, and Valrubicin), cytoskeletal disrupters (e.g., Paclitaxel and Docetaxel), epothilone agents that limit cell division by inhibiting microtubule function, inhibitor agents that block various enzymes needed for cell division or certain cell functions, histone deacetylase inhibitors (e.g., Vorinostat and Romidepsin), topoisomerase I inhibitors (e.g., Irinotecan and Topotecan), topoisomerase II inhibitors (e.g., Etoposide, Teniposide, and Tafluposide), kinase inhibitors (e.g., Bortezomib, Erlotinib, Gefitinib, Imatinib, Vemurafenib, and Vismodegib), nucleotide analogs (e.g., Azacitidine, Azathioprine, Capecitabine, Cytarabine, Doxifluridine, Fluorouracil, 5-FU, Adrucil, Carac, Efudix, Efudex, Fluoroplex, Gemcitabine, Hydroxyurea, Mercaptopurine, and Tioguanine), peptide antibiotic agents that cleave DNA and disrupt DNA unwinding/winding (e.g., Bleomycin and Actinomycin), platinum-based anti-neoplastic agents that cross link DNA which inhibits DNA repair and/or synthesis (e.g., Carboplatin, Cisplatin, Oxaliplatin, and Eloxatin), retinoids (e.g., Tretinoin, Alitretinoin, and Bexarotene), vinca alkaloids agents that inhibit mitosis and microtubule formation (e.g., Vinblastine, Vincristine, Vindesine, Vinorelbine), angiostatic inhibiting agents that inhibit cell growths or cell expansion (e.g., Axitinib (Inlyta), Bevacizumab (Avastin), Cabozantinib (Cometriq), Everolimus (Afinitor, Zortress) Lenalidomide (Revlimid), Pazopanib (Votrient), Ramucirumab (Cyramza), Regorafenib (Stivarga), Sorafenib (Nexavar), Sunitinib (Sutent), Thalidomide (Synovir, Thalomid), Vandetanib (Caprelsa), Zib-aflibercept (Zaltrap), antiangiogenic polysaccharide, aplidine (dehydrodidemnin B), sapogenins viz. 20(S)-protopanaxadiol, and 20(S)-protopanaxatriol), anti-ileus agents, pro-motility agents, immunosuppresants (e.g., Tacrolimus), blood aspect modifier agents (e.g., Vasodilator, Viagra, and Nifedipine), 3-hydroxy-3-methyl-glutaryl-CoA (HMG CoA) reductase inhibitors (e.g., Atorvastatin), and antiangiogenesis agents.

Exemplary medicants also include agents that passively contribute to wound healing such as, for example, nutrients, oxygen expelling agents, amino acids, collageno synthetic agents, Glutamine, Insulin, Butyrate, and Dextran. Exemplary medicants also include anti-adhesion agents, non-limiting examples of which include Hyaluronic acid/Carboxymethyl cellulose (seprafilm), Oxidized Regenerated Cellulose (Interceed), and Icodextrin 4% (Extraneal, Adept).

Exemplary medicants also include agents that encourage blood supply regeneration following coronary artery disease (CAD) (e.g., $VEGF_{165}$ protein, $AdVEGF_{165}$, $AdVEGF_{121}$, and $VEGF_{165}$ plasmid) or periphery artery disease (PAD) (e.g., $VEGF_{165}$ plasmid, $AdVEGF_{121}$, SB-509 (SFP-VEGF plasmid), $AdVEGF_{165}$, and Ad2-HIF1α-VP16 (WALK trial)).

Drug Release

An adjunct in accordance with the described techniques can be associated with at least one medicant in a number of different ways, so as to provide a desired effect, such as on tissue in-growth, in a desired manner. The at least one medicant can be configured to be released from the adjunct in multiple spatial and temporal patterns to trigger a desired healing process at a treatment site. The medicant can be disposed within, bonded to, incorporated within, dispersed within, or otherwise associated with the adjunct. For example, the adjunct can have one or more regions releasably retaining therein one or more different medicants. The regions can be distinct reservoirs of various sizes and shapes and retaining medicants therein in various ways, or other distinct or continuous regions within the adjuncts. In some aspects, a specific configuration of the adjunct allows it to releasably retain therein a medicant or more than one different medicant.

Regardless of the way in which the medicant is disposed within the adjunct, an effective amount of the at least one medicant can be encapsulated within a vessel, such as a pellet which can be in the form of microcapsules, microbeads, or any other vessel. The vessels can be formed from a bioabsorbable polymer.

Targeted delivery and release of at least one medicant from an adjunct can be accomplished in a number of ways which depend on various factors. In general, the at least one medicant can be released from the adjunct material as a bolus dose such that the medicant is released substantially immediately upon delivery of the adjunct material to tissue. Alternatively, the at least one medicant can be released from the adjunct over a certain duration of time, which can be minutes, hours, days, or more. A rate of the timed release and an amount of the medicant being released can depend on various factors, such as a degradation rate of a region from which the medicant is being released, a degradation rate of one or more coatings or other structures used to retains the medicant within the adjuncts, environmental conditions at a treatment site, and various other factors. In some aspects, when the adjunct has more than one medicant disposed therein, a bolus dose release of a first medicant can regulate a release of a second medicant that commences release after the first medicant is released. The adjunct can include multiple medicants, each of which can affect the release of one or more other medicants in any suitable way.

Release of at least one medicant as a bolus dose or as a timed release can occur or begin either substantially immediately upon delivery of the adjunct material to tissue, or it can be delayed until a predetermined time. The delay can depend on a structure and properties of the adjunct or one or more of its regions.

An adjunct material can be configured to have a structure that facilitates distribution of effective amounts of one or more medicants carried within the adjunct to provide a desired effect. For example, the targeted delivery of the medicants can be accomplished by incorporating the medicants into regions (e.g., reservoirs such as pores or other structures) within the adjunct formed in a pattern that allows a certain spatial distribution of the medicants upon their delivery. The medicants disposed within the reservoir can be incorporated into distinct vessels. A reservoir can include more than one type of different medicants. The one or more medicants can be eluted from the adjunct in a homogeneous manner or in heterogeneous spatial and/or temporal manner to deliver a desired therapy. The structure of the adjunct and the way in which the medicants are released therefrom can be used to influence or control tissue re-growth. Moreover, the tissue regrowth can be encouraged in certain locations at the treatment site and discouraged at other locations at the treatment site.

Implantable Adjuncts Having Adjustable Degradation Profile

As discussed above, embodiments of adjuncts can be employed for a variety of functions, such as reinforcement of tissue at a treatment site, minimizing tissue movement in and around staple puncture sites, tissue thickness compensation, and the like. This functionality relies upon one or more mechanical properties of the adjunct, such as strength (e.g., compressive strength, tensile strength), elastic modulus/stiffness, etc., remaining at or above a predetermined level after implantation in order to ensure that the functionality of the adjunct is achieved. However, after implantation, the adjunct can absorb bodily fluids (e.g., water and/or water-containing fluids). The bodily fluids can chemically react with the adjunct material (e.g., via hydrolysis) and cause the adjunct material to degrade over time, resulting in a change in the mechanical properties of the adjunct.

For a given adjunct, the change in mechanical properties as a function of time can be characterized in the form of a degradation profile. However, it can be appreciated that a surgeon may desire to adjust the degradation profile of the adjunct based on considerations such as the implantation location, type of surgery, etc. Accordingly, as discussed in detail below, embodiments of the disclosure provide compressible adjuncts having adjustable degradation profiles.

In one embodiment, a compressible adjunct kit can be provided for use with a staple cartridge and the kit can include a biocompatible adjunct material and a pretreatment fluid. The adjunct material is configured to be releasably retained on a staple cartridge body or anvil and is configured to be delivered to tissue by deployment of staples in the cartridge body. The adjunct material can be in the form of a porous polymer body. Prior to implantation, the pretreatment fluid can be applied to the adjunct material to change the adjunct material from a stock or untreated state that is configured to exhibit a first degradation profile when delivered to tissue, to a treated state that is configured to exhibit a second degradation profile when delivered to tissue. The first and second degradation profiles can differ from one another.

Figure 8:
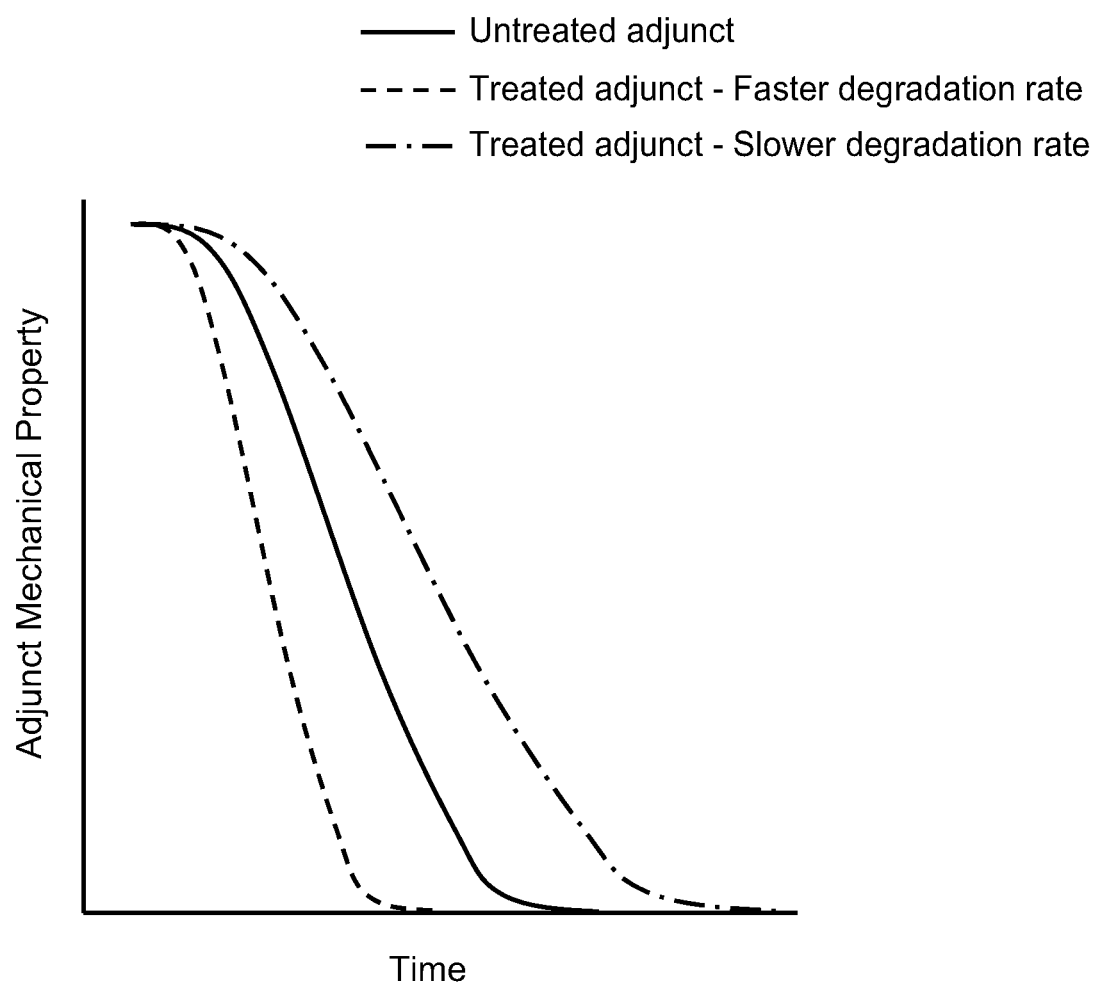
FIG. 8 is a plot illustrating exemplary degradation profiles for adjunct materials in an untreated state and a treated state after application of a pretreatment fluid.

FIG. 8 is a plot illustrating several exemplary degradation profiles, one for an untreated adjunct and two for treated adjuncts. The degradation profiles are in the form of curves representing the value of a given adjunct mechanical property as a function of time. As shown, a degradation rate of a treated adjunct, represented by the slope of the degradation profile, can be greater than or less than a degradation rate of the untreated adjunct. Embodiments of the kit can include at least one pretreatment fluid configured to increase or decrease the degradation rate. In certain embodiments, the kit can include a plurality of pretreatment fluids configured to increase or decrease the degradation rate to a predetermined degradation rate, thus allowing a user to select a pretreatment fluid configured to produce a desired degradation rate.

As discussed in greater detail below, the pretreatment fluid can employ a variety of mechanisms to increase or decrease the degradation rate of the adjunct material when delivered to tissue. In one aspect, the pretreatment fluid can increase or decrease the rate of chemical reaction between bodily fluids containing water (e.g., hydrolysis) and the treated adjunct material, as compared to the untreated adjunct. In another aspect, the pretreatment fluid can be configured to promote or inhibit absorption of bodily fluids by the adjunct material to increase or decrease, respectively, a surface area of the adjunct material that contacts, and can therefore chemically react with, the bodily fluids. By increasing or decreasing the surface area of the treated adjunct material in contact with the bodily fluids, as compared to the untreated adjunct, the degradation rate of the treated adjunct material can be increased or decreased, relative to the untreated adjunct.

In additional embodiments, compressive force can be applied to the adjunct material, prior to attachment to the staple cartridge or anvil, to alter the connectivity between pores of the adjunct material, and therefore the relative ease of fluid flow into the interior of the adjunct material. As discussed above the pores of the adjunct material can be classified as either open or closed. Open pores can allow flow of fluid therethrough while closed pores cannot. In one embodiment, compressive force applied to the adjunct material can form channels (e.g., cracks) between adjacent pores, converting closed pores to open pores. Opening the porosity in this manner can promote fluid flow through the adjunct material, increasing the surface area of the adjunct material that is available to contact bodily fluids and, therefore, increasing the degradation rate of the adjunct material. In other embodiments, compressive force applied to the adjunct material can close channels between adjacent pores, converting open pores to closed pores. Closing the porosity in this manner can inhibit fluid flow through the adjunct material, decreasing the surface area of the adjunct material that is available to contact bodily fluids and, therefore, decreasing the degradation rate of the adjunct material.

The pretreatment fluid can be applied to the adjunct material in a variety of ways. In one aspect, the adjunct material can be immersed in a vessel containing the pretreatment fluid. In another aspect, the pretreatment fluid can be applied to the adjunct material using a delivery device (e.g., a pipette, eyedropper, etc.) In certain embodiments, the pretreatment fluid is applied to the adjunct when the adjunct is separated from the staple cartridge. In other embodiments, the pretreatment fluid is applied to the adjunct when the adjunct is retained on the staple cartridge or anvil.

Certain embodiments of the pretreatment fluid can be configured to increase the degradation rate of the treated adjunct as compared to the untreated adjunct using a variety of mechanisms. In one aspect, the pretreatment fluid is configured to change (e.g., raise) the pH of any water-containing tissue or water-containing fluids adjacent to the adjunct material once implanted. As an example, the pretreatment fluid can mix with water contained in fluids contacting the adjunct material and/or water-containing fluids adjacent to the adjunct. By raising the pH at the location of the adjunct, the rate of hydrolysis of the adjunct material can be increased, thereby increasing the degradation rate of the treated adjunct. Examples of pretreatment fluids effective to increase the pH include, but are not limited to, fluids including one or more salts, bicarbonates, or other buffered aspects. In an embodiment, the pretreatment fluid is a solution of sodium chloride and water (e.g., saline solution).

In another aspect, the pretreatment fluid is configured to make the adjunct material more hydrophilic. As an example, the pretreatment fluid can form a coating or film on at least a portion of the surfaces of the adjunct material (e.g., exterior surfaces, interior surfaces of pores, etc.) In general, when water contacts the surface of a material that is hydrophilic, the water tends to spread out or "wet" the surface. As the degree of hydrophilicity of a surface increases, the area of contact between a given volume of water and the surface increases. Therefore, increasing the hydrophilicity of the adjunct can increase the degradation rate of the adjunct material due to increasing the area of contact between the adjunct material and water and/or water-containing bodily fluids. Examples of pretreatment fluids effective to increase the hydrophilicity of the adjunct material include, but are not limited to, wetting agents or surfactants such as loosely cross-linked polymers.

In further embodiments, cross-linking can be employed to increase the hydrophilicity of the adjunct material, alone or in combination with a pretreatment fluid. For example, the adjunct material can be physically cross-linked (e.g., irradiated by ultraviolet (UV) and gamma radiation and dehydrothermal treatment) or chemically cross-linked (e.g., use of chemical cross-linker(s), such as genipin and glutaraldehyde). In certain embodiments, the pretreatment fluid can include one or more chemical cross-linkers. Non-limiting examples of the chemical cross-linkers include bi-/multi-functional molecules, which bridge free carboxylic acid groups, amino groups, and hydroxyl groups between adjacent polymer molecules (e.g., glutaraldehyde, polyepoxides, and isocyanates), chromium sulphate, aldehydes, and isocyanates.

In alternative embodiments, the pretreatment fluid can be configured to decrease the degradation rate of the adjunct material as compared to the untreated adjunct using a variety of mechanisms. In one aspect, the pretreatment fluid can configured to make the adjunct material more hydrophobic. As an example, the pretreatment fluid can form a coating or film on at least a portion of the surfaces of the adjunct material (e.g., exterior surfaces, interior surfaces of pores, etc.) In general, when water contacts the surface of a material that is hydrophobic, the water tends to form beads, rather than spreading out or "wetting" the surface. As the degree of hydrophobicity of a surface increases, the area of contact between a given volume of water and the surface increases. Therefore, increasing the hydrophobicity of the adjunct can decrease the degradation rate of the adjunct material due to decreasing the area of contact between the adjunct material and water and/or water-containing bodily fluids. Examples of such pretreatment fluids include, but are not limited to, silicones and other materials suitable for increasing the hydrophobicity of surfaces of the adjunct material.

In another aspect, the pretreatment fluid can be configured to form a coating that is deposited on at least a portion of the surfaces of the adjunct (e.g., exterior surfaces, interior surfaces of pores, etc.) in the treated state. The coating forms a barrier that inhibits contact between the adjunct material and water and/or water-containing bodily fluids. That is, the water or water-containing fluids are required to penetrate the coating (e.g., via diffusion) before reacting with and degrading the adjunct material. As penetration of the coating is not instantaneous and requires some time to accomplish, the presence of the coating delays the onset of hydrolysis and increases the time to achieve a given amount of degradation, thereby decreasing the degradation rate. Examples of such pretreatment fluids can include, but are not limited to, oils (e.g., mineral oils, food grade oils), greases, biocompatible lubricants, and perfluoropolyether (PFPE)).

In a further aspect, the pretreatment fluid is configured to form a sealant that seals at least a portion of the pores of the porous polymer body, inhibiting ingress of water or water-containing bodily fluids within the bulk of the adjunct material. As an example, the sealant formed by the pretreatment fluid can be positioned on the surface and/or the interior of the adjunct material so as to partially and/or completely obstruct respective flow passageways leading from the surface of adjunct material to pores within the bulk of the adjunct material. Therefore, the sealant can decrease the degradation rate of the adjunct material due to decreasing the area of contact between the adjunct material and water and/or water-containing bodily fluids. Examples of such pretreatment fluids can include, but are not limited to, oils (e.g., mineral oils, food grade oils), greases, biocompatible lubricants, and other highly viscous materials capable of blocking fluid flow into pores of the adjunct material, and perfluoropolyether (PFPE)).

In another aspect, the pretreatment fluid is configured to react with the adjunct material (e.g., via a substitution reaction) to change a terminal functional group of at least a portion of a polymer chains forming the porous polymer body in the treated state as compared to the untreated state. The difference in terminal functional groups inhibits contact between the polymer adjunct material and water or water-containing bodily fluids. Therefore, the terminal functional group can decrease the degradation rate of the adjunct material due to decreasing the area of contact between the adjunct material and water and/or water-containing bodily fluids. Examples of such pretreatment fluids can include, but are not limited to, saline and acids (e.g., carbonic acid).

As an additional example, the pretreatment fluid can configured to terminate at least a portion of a plurality of polymer chains of the porous polymer body. As a result, an average length of the plurality of polymer chains of the polymer body in the treated state is less than an average length of the plurality of polymer chains of the polymer body in the untreated state. The decrease in average chain length decreases the area of contact between the polymer adjunct material and water, thereby decreasing the rate of degradation of the adjunct material.

As indicated above, the adjunct can be used with a staple cartridge or anvil for treating tissue. Prior to implantation, the adjunct material can be treated with the pretreatment fluid, either prior to or after attachment to a staple cartridge, e.g., such as staple cartridge 102 shown in FIG. 6 or anvil (e.g., upper jaw surface 34) shown in FIG. 2. As a result, the pretreatment fluid can be present on at least the surface of the adjunct material. In certain embodiments, the pretreatment fluid can also flow from the surface of the adjunct material to the interior or bulk of the adjunct material via open pores. Once properly treated, and with the treated adjunct material releasably retained on the anvil or staple cartridge and the cartridge disposed within a jaw of a surgical staple, such as stapler 10 or FIG. 1, the device can be manipulated to engage tissue between the jaws 32, 34 and to actuate the device thereby firing staples through the adjunct material and the tissue to secure the adjunct material to the tissue, as shown for example in FIG. 7.

Once implanted, the pretreated adjunct material can interact with water adjacent to the adjunct material. Such water can be in the form of water alone or a mixture with other bodily fluids. Additionally, the water can be located at the surface of the adjunct material and within at least a portion of the interior of the adjunct material (e.g., via flow through fluid passageways such as open pores in fluid communication with the surface of the adjunct material).

The configuration of the pretreatment fluid dictates whether the pretreatment fluid increases or decreases the degradation rate of the adjunct material. Embodiments of the pretreatment material that are configured to increase the degradation rate of the adjunct material can do so by increasing the rate of chemical reaction (e.g., hydrolysis) between the adjunct material and the water or by increasing the area of contact between the water and the adjunct material. In one example, the pretreatment fluid can mix with water that contacts surfaces of the adjunct (e.g., exterior surfaces or interior surfaces of pores). The mixture of pretreatment fluid and water can possess a higher pH than the water alone and accelerate the rate of hydrolysis reactions with the adjunct material. In another example, the pretreatment fluid can form a coating or film on the surfaces of the adjunct material (e.g., exterior surfaces or interior surfaces of pores) that increases the hydrophilicity of these surfaces. The increased hydrophilicity causes water contacting these surfaces to spread out and wet the surfaces, increasing the surface area of contact between the adjunct material and the water, thereby increasing the degradation rate of the adjunct material.

Embodiments of the pretreatment material that are configured to increase the degradation rate of the adjunct material can do so by decreasing the area of contact between the water and the adjunct material, via physical or chemical mechanisms. Pretreatment fluids that physically decrease the area of contact can include coatings or sealants. Coatings of the pretreatment fluid can be formed by flow of the pretreatment fluid onto surfaces of the adjunct material (e.g., exterior surfaces or interior surfaces of pores). Once present on the surfaces of the adjunct material, the coatings can form a physical barrier to interaction between the water and the adjunct material. The pretreatment fluid can form sealants by flowing to and residing between adjacent surfaces of the adjunct material that function as fluid passageways between the exterior surface of the adjunct material and the interior of the adjunct material. Once present in the flow passageways, the sealants can block flow of water therethrough, isolating interior regions of the adjunct material from interaction with water. Alternatively, the pretreatment fluid can react with the polymer chains forming the adjunct material to sever these polymer chains, physically reducing the length of the polymer chains and, therefore, reducing the area of the adjunct material that can contact the water. Pretreatment fluids that chemically decrease the area of contact can include hydrophobic agents and substitution agents. Hydrophobic agents can form a coating or film on the surfaces of the adjunct material (e.g., exterior surfaces or interior surfaces of pores) that increases the hydrophobicity of these surfaces. The increased hydrophobicity causes water contacting these surfaces to ball up, rather than spreading out to wet the surfaces. Substitution agents can chemically react with the polymer chains forming the adjunct material, changing the terminal group of the polymer chains to a functional group that inhibits interaction of water therewith.

Implantable Adjuncts Having Compressive Properties that Degrade Based Upon Healing Progression When implanting an adjunct adjacent to the cut tissue, one function of the adjunct can be application of pressure to the tissue (e.g., a cut line) when stapled thereto to facilitate the healing process (e.g., hemostasis). As healing progresses, it can be further desirable to reduce the pressure (compressive pressure) applied to the tissue in order to facilitate formation of blood vessels (vascularization). Existing adjuncts can be configured to degrade as a function of time, and therefore decrease the pressure applied to tissue, by degradation due to chemical reaction with water (hydrolysis). However, such degradation and reduction in pressure is not directly correlated to tissue healing. Thus, the level of pressure maintained by existing degradable adjuncts at a given time can be inappropriate for the degree of healing progression at that time and, actually inhibit, rather than facilitate the healing process.

Accordingly, in further embodiments, implantable adjuncts are provided that can be configured to exhibit a decrease in stiffness after implantation. The decrease in stiffness can result from degradation of the adjunct material due to chemical reaction with physiologic elements released during the healing process. When stapled to the tissue, the decrease in stiffness further results in a decrease in pressure applied by the adjunct to the tissue. In this manner, the applied pressure is correlated to the advancement of healing progression of the tissue, rather than merely time exposed to water.

In one embodiment, a biocompatible adjunct material is configured to be releasably retained on a staple cartridge and is configured to be delivered to tissue by deployment of staples in the staple cartridge. The adjunct material can be in the form of a porous polymer body exhibiting a first compressive stiffness that is approximately constant during a first time period from contact with the tissue. The porous polymer body can further exhibit a second compressive stiffness following the first time period that is less than the first compressive property. The second compressive property can decrease with time due to interaction (e.g., chemical reaction) with at least one physiological element released from the tissue during healing progression of the tissue. In other words, as the healing process progresses, physiological elements released from the tissue during different stages of the healing process can interact with the adjunct thereby causing the compressive properties of the adjunct to change. As discussed in greater detail below, examples of interaction of the porous polymer body with the at least one physiological element can include oxidation, enzyme-catalyzed hydrolysis, and change of pH adjacent to the adjunct.

The first time period represents a time duration prior to substantive reaction of the porous polymer body with the at least one physiological element. That is, a time duration over which any change in the first compressive stiffness is negligible (e.g., less than about 5%, less that about 4%, less than about 3%, less than about 2%, less than about 1%, etc.) In contrast, the second time period can represent a time duration during which reaction of the porous polymer body with the at least one physiological element occurs.

In one embodiment, the interaction of the porous polymer body with the at least one physiological element results in enzymatic degradation due to progression of the healing response and the body's introduction of the at least one physiological element into the healing site as the wound is remodeled.

As indicated above, in one embodiment, the interaction between the porous polymer body and the at least one physiological element is an oxidation reaction, where the at least one physiological element is an oxygen containing enzyme. In general, wound healing can be divided into four phases, hemostasis, inflammation, proliferation, and remodeling, and nearly every phase in the wound healing process can require oxygen, as outlined below.

Healing tissue requires energy, which is generated from oxidative metabolism of glucose. In aerobic metabolism of glucose, cells use oxygen to generate adenosine triphosphate (ATP), which fuels a majority of cellular processes during wound healing. Thus, healing tissue has increased oxygen demand. Increased oxygen consumption in turn causes hypoxia and activates the initial steps of the healing process by boosting activity of reactive oxygen species.

During the inflammatory phase of healing progression, the area of inflammation is a site for significant production of reactive oxygen species. In one aspect, this production is due to the occurrence of phagocytosis, the ingestion of cells or other materials by phagocytes as a defense against infection and invasion by foreign substances. The presence of reactive oxygen species further stimulate other functions necessary for wound repair, such as recruitment and activation of inflammatory cells such a leukocytes (white blood cells) at the wound site and the activation of fibroblasts. Examples of leukocytes include neutrophils, basophils, eosinophils, lymphocytes, monocytes, and macrophages. These inflammatory cells are also able to produce the at least one physiological element in the form of highly reactive oxygen species. Examples of classes of highly reactive oxygen species can include at least one of oxygen containing enzymes, free radicals, superoxides, and peroxides. Specific examples of the reactive oxygen species can include at least one of $O^{2-}$, $H_2O_2$, NO, and HOCl. At this time, a set of growth factors can be released that stimulate and attract the components of wound healing, such as wound leukocytes and fibroblasts. Hydrogen peroxide ($H_2O_2$) can be a mediator of these interactions. As wound healing progresses, cell proliferation and migration occur due to redox signaling of the reactive oxygen species. The last step or phase of wound healing is remodeling. During remodeling, the wound gains tensile strength, and the collagen fibers contract so the wound shrinks. The most prominent mediators of collagen processes are compounds released by macrophages, keratinocytes, endothelial cells, and fibroblasts/fibrocytes, all of which are dependent on oxygen.

In further embodiments, reactive oxygen species can be directed to a wound healing site from other regions in the body. In general, cells typically consume oxygen during their function. For the body to keep them alive it typically provides the oxygen via biologic processes like hemoglobin transport. As the body sees more cells in a region, angiogenesis grows blood pathways to the site to supply nutrients and oxygen to the site to sustain the cellular populations.

From the forgoing, it can be appreciated that the healing process results in the production and/or attraction of reactive oxygen species to the site of wound healing. These reactive oxygen species can participate in oxidation reactions with the polymer adjunct material to cause polymer chain scission and contribute to degradation of the adjunct. In particular, $O^2$ can accelerate the degradation of polymers such as aliphatic polyesters by cleavage of ester bonds via nucleophilic attack. The oxygen-induced degradation chemically breaks down the polymer adjunct material, causing it to weaken and become less stiff, thus changing the applied pressure (e.g., compressive force) applied to the tissue. Because the concentration of reactive oxygen species available to react with the polymer adjunct material is a function of the healing process, the degree of oxygen-induced degradation of the polymer adjunct material, and therefore the pressure applied to the tissue by the adjunct, is also a function of the healing process.

In further embodiments, enzyme-catalyzed hydrolysis can contribute to degradation of the polymer body and attendant reduction in stiffness of the adjunct material. As an example, the adsorption and rate of hydrolysis reaction can be affected by (i) the physiochemical properties of the polymer body (e.g., molecular weight, chemical composition, crystallinity, surface area, etc.), (ii) the characteristics of a specific enzyme (e.g., activity, stability, local concentration, amino acid composition, and three-dimensional conformation), and (iii) medium conditions such as pH and temperature. The presence of stabilizers, activators, and/or inhibitory products in the local environment adjacent to the adjunct (e.g., resulting from degradation of the adjunct material or leaching out of processing additives) can also affect enzyme-catalyzed reactions by influencing enzyme adsorption and activity. Examples of such enzymes can include, but are not limited to, hydrolyzes such as proteases, esterases, glycosidases, phosphatases, and other suitable hydrolytic enzymes.

In additional embodiments, chemical modification of the polymer body (e.g., cross-linking, removal or introduction of chemical groups into the polymer chain) can affect the enzymatic degradation rate. Notably, depending on the degree of chemical modification, it can compromise the ability of the enzyme to recognize the modified polymer body. As an example, lysozyme, the enzyme responsible for degradation of peptidoglycan and chitin materials, exhibits low activity towards chitosans with high degrees of deacetylation or cross-linked chitosan. Examples of such enzymes can include, but are not limited to, lysozyme.

In other embodiments, degradation can be linked to other physiologic chemical changes in situ. For example, pH is one of the most impacted changes within the local chemical environment due to healing progression of infection development. The pH value adjacent to a wound directly and indirectly influences at least a portion of, and up to all of, the biochemical reactions taking place in the process of wound healing. As an example, the surface pH of a wound plays an important role in wound healing, as it helps control infection and increase anti-microbial activity, oxygen release, angiogenesis, protease activity, and biological toxicity. Accordingly, pH value can affect regular cellular events in wound healing.

Additionally, wounds with a high alkaline pH have a lower healing rate in both acute and chronic wounds as compared to wounds with a pH closer to neutral. That is, wound healing progression decreases when pH is elevated to alkaline levels. The environment of acute, as well as chronic wounds, progresses from an alkaline state to a neutral state, and then to an acidic state, when healing begins.

Accordingly, embodiments of the adjunct can be configured to adopt the second stiffness in response to a decrease in pH in the local environment adjacent to the polymer body resulting from the presence of the at least one physiological element. As discussed above, the pH of water or water-containing biological material participating in hydrolysis reactions can influence the rate of hydrolysis. Specifically, the rate of hydrolysis can decrease with decreasing pH. As the pH in the local environment of a wound decreases with healing progression, it can be expected that the reduction in pH will also be experienced by water and water-containing fluids participating in hydrolysis reaction with the adjunct material. Therefore, the rate of hydrolysis of the adjunct material, and relative contribution of hydrolysis to degradation of the adjunct material can decrease over time as compared to the relative contribution of oxidation to degradation of the adjunct material. However, it can be appreciated that the overall rate of degradation of the adjunct material resulting from combination of oxidation and hydrolysis processes can exceed the rate of degradation due to oxidation alone.

As indicated above, the adjunct can be used with a staple cartridge or anvil of the surgical stapler 10 for treating tissue e.g., such as staple cartridge 102 shown in FIG. 6 or anvil (e.g., upper jaw surface 34) shown in FIG. 2. During implantation, the adjunct material can be delivered to tissue by deployment of staples in the staple cartridge body, securing the adjunct material to the tissue and causing the adjunct material to apply pressure (e.g., compressive pressure) to a wound (e.g., a cut line).

In use, the healing process occurs within the tissue coupled to the adjunct material. The healing process begins with hemostasis, where flow of blood from the wound is stopped. In general, it is beneficial for the adjunct to apply a relatively high pressure (compressive pressure) to the wound to facilitate hemostasis. As discussed above, the adjunct can be compressed (e.g., by upper and lower jaws 22, 34 when delivered to the tissue by deployment of staples and can expand when released. Accordingly, the adjunct material can be configured to exhibit a first stiffness in compression such that, when the adjunct is deployed, a compressive pressure exerted by the adjunct when expanded against the tissue is sufficiently high to assist hemostasis of the tissue.

The adjunct can be further configured to maintain the first stiffness at an approximately constant level during a first time period from contact with the tissue. That is, the adjunct material can experience little to no degradation due to reaction (e.g., oxidation, enzyme-catalyzed hydrolysis, etc.) with bodily fluids such as water or water-containing fluids during the first time period. By maintaining the first stiffness at an approximately constant level during the first time period, the compressive pressure applied by the adjunct material to the tissue is also maintained at an approximately constant level.

The adjunct material can be configured to maintain the first stiffness over the first time period in a variety of ways. As discussed above, in one aspect, the adjunct material can be treated, as discussed above, with a pretreatment fluid to reduce the rate of degradation of the adjunct material. In another aspect, the adjunct material can be mechanically compressed to close at least a portion of the porosity of the adjunct material to inhibit flow of bodily fluids. It can be appreciated that one or more other mechanisms for reducing the rate of degradation of the adjunct material can be employed, alone or in any combination with those discussed above, can be employed without limit.

As healing progression continues into the inflammation, proliferation, and remodeling stages, it can be desirable to reduce the compressive pressure applied by the adjunct material to the tissue to facilitate formation of blood vessels. Accordingly, the adjunct material can be configured to exhibit a second stiffness, less than the first stiffness, during a second time period following the first time period.

As an example, during the second time period, these later healing stages can occur and the tissue can release the at least one physiological element to facilitate healing. For example, the at least one physiological element can include a reactive oxygen species. While the reactive oxygen species is produced to provide energy for the healing process, it can also interact with the adjunct material to cause degradation. Examples of such interactions can include oxidation via reaction with the reactive oxygen species, hydrolysis that is catalyzed by an enzyme (e.g., oxygen-containing enzyme), and change of pH resulting from the presence of the at least one physiological element in the fluid environment local to the adjunct material. Oxidation can contribute to degradation of the adjunct material by polymer chain scission, while enzyme-catalyzed hydrolysis can contribute to degradation by chemical breakdown of the polymer adjunct material. pH can contribute to degradation by influencing the rate of degradation, where the increased rate of degradation can be greatest when the pH is relatively high (e.g., alkaline relatively early within the healing process). A least oxidation can be a function of the healing process, as it depends upon the concentration of reactive oxygen species e produced during healing. As a result, degradation of the adjunct material can be a function of the healing progression, which results in the adjunct material exhibiting a second stiffness that is less than the first stiffness, that decreases with advancement of the healing process. Beneficially, as noted above, the reduction in stiffness of the adjunct material from the first stiffness to the second stiffness can promote vascularization.

Tissue Thickness Compensating Adjunct Having Regions of Differential Expansion

As discussed above, in certain embodiments, adjuncts can be configured to compensate for variations in tissue thickness when stapled to tissue, exhibiting an uncompressed (un-deformed), or pre-deployed, height, and being configured to deform to one of a plurality of compressed (deformed), or deployed, heights. It can be appreciated that leakage of bodily fluids (e.g., blood, air, gastrointestinal fluids, etc.) can occur when staples penetrate the adjunct and tissue. Notably, penetration of the adjunct the staples can form holes in the adjunct that are larger than the diameter of the staple legs. Furthermore, when tissue is cut, prior to onset of hemostasis, blood can flow along a cut line. Accordingly, it can be desirable to employ the adjunct material to seal staple puncture holes and/or apply pressure to the staple line to facilitate hemostasis.

In further embodiments discussed in detail below, tissue thickness compensating adjuncts are provided that are formed from a material that swells when exposed to moisture and that have a structure that varies in thickness and/or pressure as a function of position within the adjunct. As an example, predefined portions of the adjunct are configured to permit or restrain expansion of the adjunct, thus altering the sealing pressure applied to the tissue at those predefined portions of the adjunct. In one aspect, portions of the adjunct adjacent to respective incipient staple lines, where staple legs are intended to penetrate the adjunct material, can be configured expand when exposed to moisture as compared to portions of the adjunct distanced from the incipient staple lines. This expansion of the adjunct can urge the adjunct material in contact with the staple legs and sealing the staple holes. In another aspect, portions of the adjunct adjacent to an incipient cut line, where a knife is expected to pass and cut the tissue and adjunct, can be configured to expand when exposed to moisture, as compared to portions of the adjunct distanced from the incipient cut line. This expansion of the adjunct can allow the adjunct to apply a compressive pressure to the cut line and/or regions of the tissue adjacent to the cut line to promote hemostasis.

Figure 9:
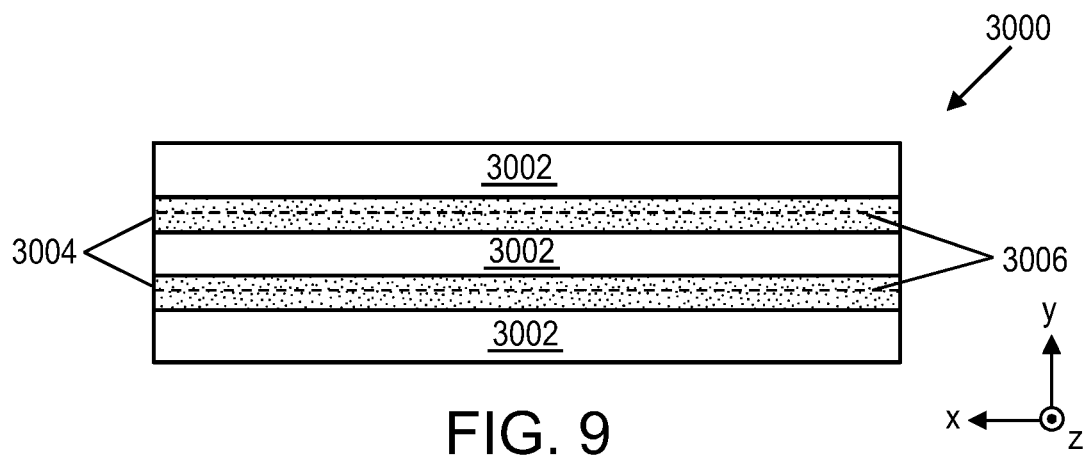
FIG. 9 is a schematic diagram illustrating a top view of an upper tissue contacting surface of one exemplary embodiment of a tissue thickness compensating adjunct in an un-deformed or pre-deployed state configured for sealing staples along a staple line.

FIG. 9 is a schematic diagram illustrating a top view (e.g., an x-y plane) of an upper tissue contacting surface of one exemplary embodiment of a tissue thickness compensating adjunct 3000 in the un-deformed or pre-deployed state. The adjunct 3000 includes at one or more first portions 3002 and one or more second portions 3004. While the adjunct 3000 is configured to be releasably retained on a staple cartridge or anvil of a stapling assembly, the adjunct 3000 is shown in isolation for clarity.

The first portions 3002 of the adjunct 3000 can be formed from a first material that is configured to exhibit a first expansion behavior in response to receipt of a unit volume of fluid. The second portion 3004 of the adjunct 3000 can be configured to exhibit a second expansion behavior, different from the first expansion behavior, in response to receipt of the unit volume of fluid. The expansion behavior can include, but is not limited to, expansion volume and expansion rate. In certain embodiments the volume of expansion and/or rate of expansion given by the second expansion behavior of the second material is greater than a corresponding volume of expansion and/or rate of expansion given by the first expansion behavior of the first material.

The first portions 3002 can be formed from a biocompatible porous polymer material, as discussed above. In contrast, the second portions 3004 can be formed from a swellable material that is different from the biocompatible porous polymer material of the first portions 3002. Examples of swellable materials can include, but are not limited to, hydrogels, a low molecular weight polymers (e.g., polymers having an average molecular weight sufficient to be cleared from the patient's body, such as less than about 30,000 kDa), polymers having a relatively low degree of cross-linking.

It can be appreciated that alternative embodiments of the adjunct can be configured to change the relative expansion characteristics (e.g., volume of expansion, rate of expansion, etc.) of the first and second portions from those discussed above. For example, the volume of expansion and/or rate of expansion of the first portions of the adjunct can be greater than that of the second portions in response to receipt of approximately the same volume of moisture. Furthermore, while not shown, additional embodiments of the adjunct can include greater than two regions, each configured to swell by different respective amount in response to receipt of approximately the same volume of moisture.

As noted above, a common problem encountered when employing surgical staples with adjuncts is seepage of one or more fluids (e.g., water, blood, air, gastrointestinal fluids, etc.) through the openings formed by the staples, even after the staple is fully formed. Accordingly, in further embodiments of the adjunct 3000, the relative placement of the first and second portions 3002, 3004 can be configured to apply pressure to staples along staple lines to seal holes formed within the adjunct by staples. As shown in the top view of FIG. 9, incipient staple lines 3006 extend along the length of the adjunct 3000 (e.g., in the longitudinal or x-direction). The second portions 3004 are approximately aligned with (e.g., approximately parallel to) the incipient staple lines 3006 and have a width greater than the incipient staple lines 3006. Under circumstances where multiple incipient staple lines 3006 are present, they can be separated from one another in a width direction (e.g., the y-direction) by the first portions 3002 and extend in a longitudinal direction of the adjunct (e.g., the x-direction), aligned with respective staple lines 3006.

Figure 10:
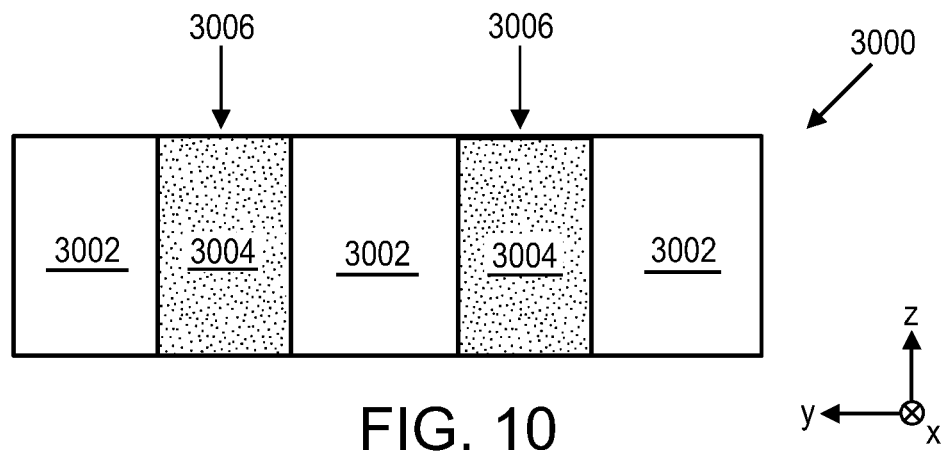
FIG. 10 is a schematic diagram illustrating an end-on view of the tissue thickness compensating adjunct of FIG. 9 in the un-deformed or un-deployed state.

FIG. 10 is an end-on view (e.g., a y-z plane) of the adjunct 3000 of FIG. 9. As shown, the second portions 3004 can extend through an entirety of the thickness (e.g., z-direction) of the adjunct 3000.

Figure 11:
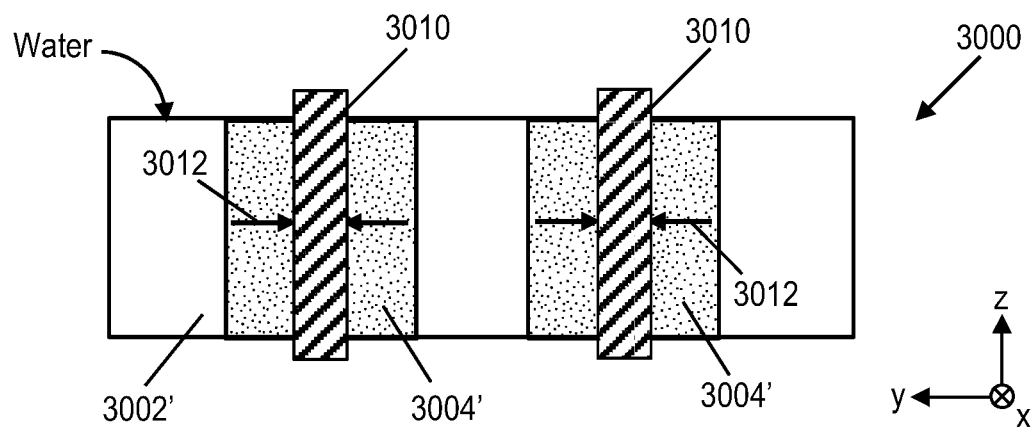
FIG. 11 is a schematic diagram illustrating an end-on view of the tissue thickness compensating adjunct of FIG. 9 in a deformed or deployed state where expanded portions of the adjunct exert a sealing pressure against staples extending therethrough.

Prior to deployment, and receipt of water or other physiological fluids, the adjunct 3000 has a first shape. Once implanted, and upon receipt of water or other fluids, the second portions 3004 expand to form corresponding expanded second portions 3004" and adopt a second shape, different from the first shape, as shown in FIG. 11. As a result, the of expansion, the second portions 3004 exert a compressive force or pressure (arrows 3012) on the staples 3010 thereby partially or substantially completely sealing the holes formed through the adjunct 3000 by passage of the staples 3010 therethrough. The expansion behavior of respective expanded second portions 3004' can be the same or different as a function of position along the staple line 3006 (e.g., along the x-direction).

Figure 12:
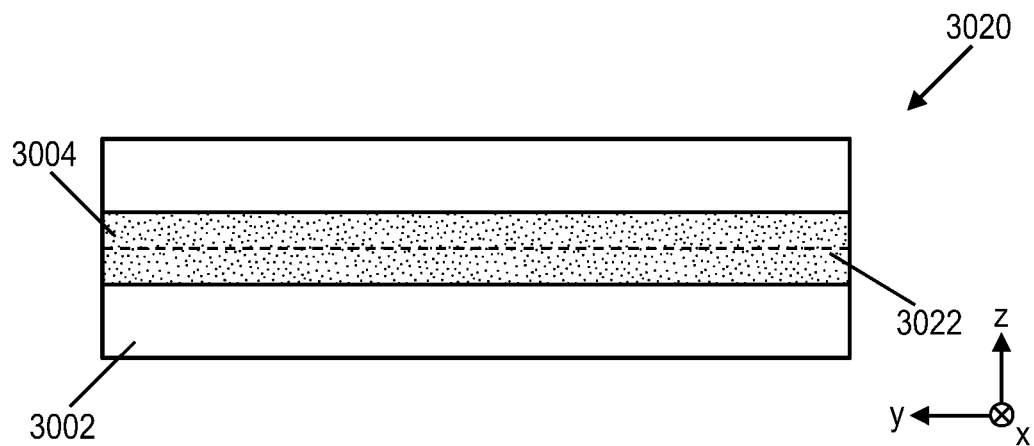
FIG. 12 is a schematic diagram illustrating a top view of an upper tissue contacting surface of another exemplary embodiment of an adjunct configured to apply pressure along a tissue cut line.
Figure 13:
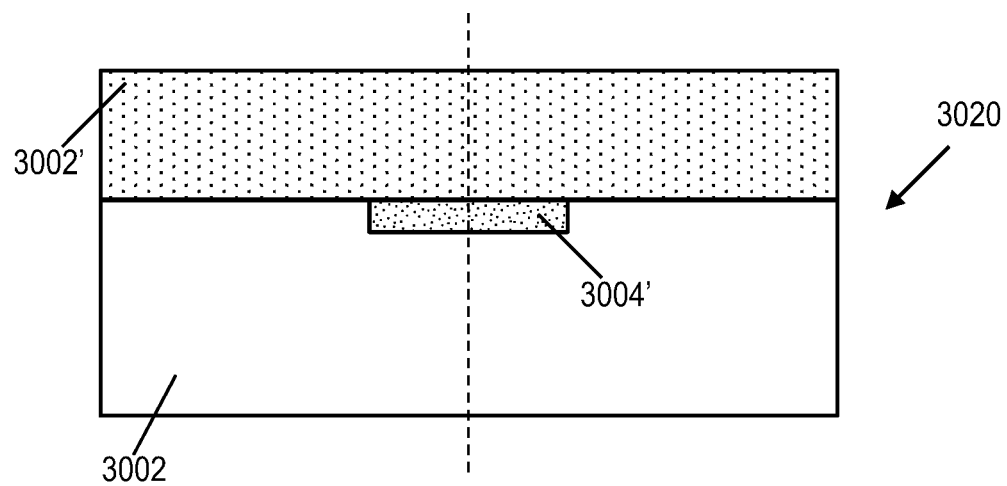
FIG. 13 is a schematic diagram illustrating an end-on view of the tissue thickness compensating adjunct of FIG. 12 in the un-deformed or un-deployed state.
Figure 14:
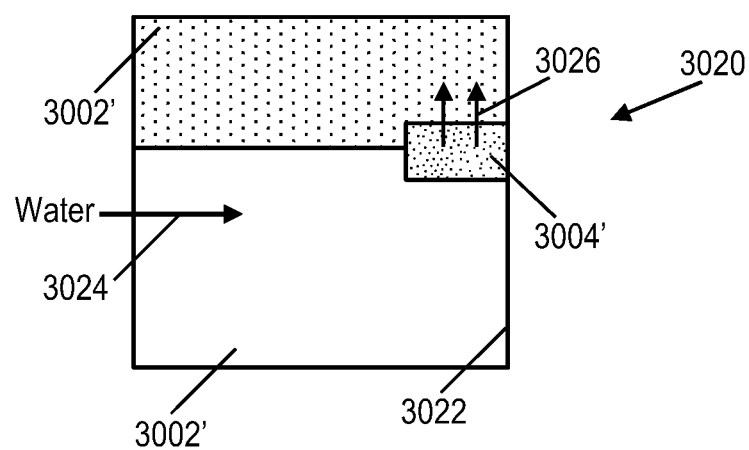
FIG. 14 is a schematic diagram illustrating an end-on view of the tissue thickness compensating adjunct of FIG. 13 in the deformed or deployed state.

In another embodiment, the relative placement of the first and second portions 3002 and 3004 can be configured such that expansion of at least one of the first and second portions 3002, 3004 exerts pressure along and/or adjacent to a tissue cut line that is sufficient to provide hemostasis. FIG. 12 is a schematic diagram illustrating a top view of an upper tissue contacting surface another exemplary embodiment of a tissue thickness compensating adjunct 3020 in the un-deformed or pre-deployed state. FIG. 13 is an end-on view of the adjunct 3020 of FIG. 12. FIG. 14 is an end-on view of the adjunct 3020 in the deformed or deployed state. While the adjunct 3000 is configured to be releasably retained on a staple cartridge or anvil of a stapling assembly, the adjunct 3020 is shown in isolation for clarity.

As shown in FIG. 12 and FIG. 13, similar to the adjunct 3000, the adjunct 3020 includes first and second portions 3002, 3004. However, in contrast to the adjunct 3000, the second portion(s) 3004 overlie at least the first portion(s) 3002 on and/or adjacent to an incipient tissue cut line 3022. In other embodiments, the second portion(s) can overlie substantially the entire first portion(s). The adjunct 3020 can be positioned on the staple cartridge of a stapling assembly, with the first portion(s) 3022 spaced a distance from an expected path of a knife 36, as shown in FIG. 3 that defines the incipient tissue cut line 3022 and the second portion(s) 3004 positioned on or adjacent to the knife path/incipient tissue cut line 3022. So configured, receipt of water or other fluids by the adjunct 3020 (arrow 3024) results in expansion of the second portion(s) 3004 relative to the first portion(s) 3002 to form expanded second portion(s) 3004', as shown in FIG. 14. The expanded second portion(s) 3004' exert pressure (arrows 3026) along the cut line 3022 to promote hemostasis. The expansion behavior of respective expanded second portions 3004' can be the same or different as a function of position along the knife path/incipient tissue cut line 3022.

In further embodiments of the adjuncts 3000, 3020, the second portions 3004 can be formed from a porous, solid material and housed in a compressed state within a fluid soluble capsule. The capsule can be configured to degrade relatively quickly in response to contact with water and/or other physiological fluids after a predetermined time period (e.g., on the order of seconds to minutes) for release of the second portions therefrom. Beneficially, such encapsulation provides for time-release control of pressure applied by the adjuncts 3000, 3020 to tissue.

In other embodiments, tissue thickness compensating adjuncts can be configured to degrade over time, providing a short-term mechanism for compression of tissue. As discussed in greater detail below, such adjuncts can be combined with other mechanisms that provide comparatively longer-term compression (e.g., staples). Together, these short- and long-term compression mechanisms can promote tissue healing.

In general, the mechanical properties of bioabsorbable adjunct materials change (e.g., reduce) over time as the degree of degradation of the adjunct increases. In one embodiment, the adjunct 3020 can be configured to degrade at a rate that maintains sufficient compression (e.g., by the expanded second portions 3004') to allow the body to coagulate/clot bleeding within the region of the cut line 3022. Compressive pressure provided by staples can be provided to further reinforce the cut line for a longer time duration and lower magnitude, as compared to that provided by the adjunct. Beneficially, the relative high compressive pressure provided in the short-term by the adjunct 3020 facilitates clotting while the relatively lower compressive pressure provided in the long-term by the staples provides reinforcement without restricting flow of blood to the cut line 3022.

Figure 15:
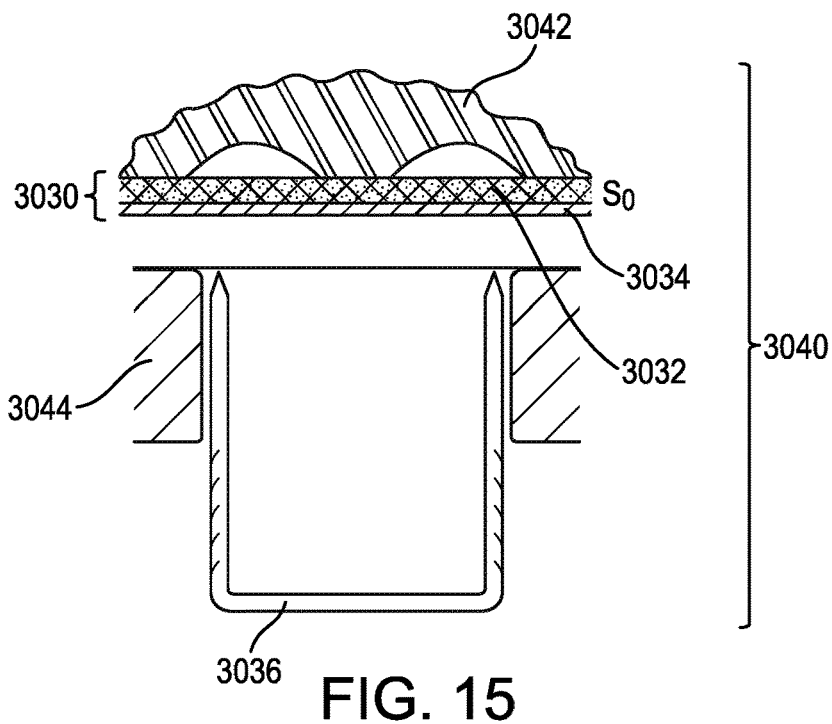
FIG. 15 is a schematic diagram illustrating a side cross-sectional view of a stapling assembly in a pre-firing configuration including an anvil and staple cartridge with another embodiment of a tissue compensating adjunct mounted on an anvil, the adjunct being configured to work in combination with staples fired from the staple cartridge to inhibit retraction of the adjunct from contact with the tissue after staple firing.

In another embodiment, a tissue thickness compensating adjunct 3030 is provided and is configured to work in combination with staples 3036 to inhibit retraction of the adjunct 3030 from contact with the tissue 3038 after expansion. FIG. 15 is a schematic diagram illustrating a side cross-sectional view of a stapling assembly 3040 in a pre-firing configuration that includes a first jaw having an anvil 3042 (shown in part) opposite a staple cartridge 3044 housing a plurality of staples (only one staple 3036 is shown). The adjunct 3020 is positioned on the anvil 3042 and includes one or more first portions 3032 underlying one or more second portions 3034. The first portion 3032 contacts the anvil 3042 and the second portion 3034 is spaced apart from the anvil 3042 and faces tissue. The adjunct 3030 has a total initial thickness $s_o$ in this pre-firing configuration. As shown, the first and second portions 3032, 3034 are generally planar. However, other non-planar configurations can be employed without limit. Additionally, while the embodiment of FIG. 15 illustrates the adjunct positioned on the anvil, in alternative embodiments, the adjunct can be positioned on the staple cartridge.

Figure 16:
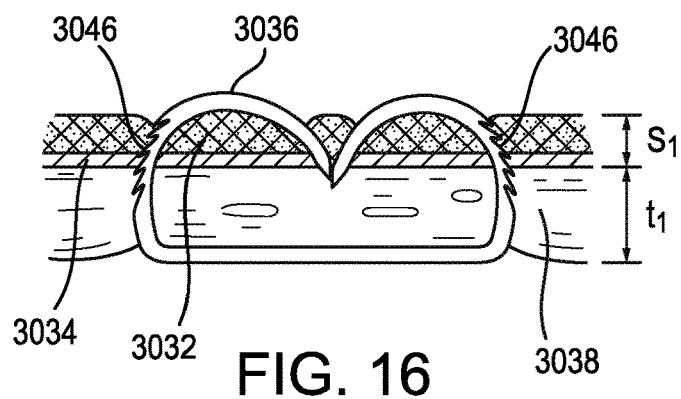
FIG. 16 is a schematic diagram illustrating the stapling assembly and adjunct of FIG. 15 immediately after firing of a staple from the staple cartridge, through the adjunct and tissue, and release of the adjunct and tissue from the stapling assembly.

In operation, as shown in FIG. 16, the tissue 3038 is clamped between the anvil 3042 and the staple cartridge 3044 and one or more staples 3036 are fired from the staple cartridge, through the adjunct 330, and into the tissue 3038 to thereby staple the adjunct 3030 to the tissue 3038. As further illustrated in FIG. 17, the adjunct 3030 and tissue 3038 are subsequently released from the stapling assembly 3040 after staple firing. The total thickness of the adjunct 3030 after release from the stapling assembly 3040 increases from the initial thickness $s_o$ to an implanted thickness $s_1$ due to removal of the clamping force applied by the stapling assembly 3040. The tissue 3038 has a thickness $t_1$.

After being stapled to the tissue 3038, the adjunct receives a unit volume of fluid (e.g., water and/or other physiological fluids). At least one of the first and second portions 3032, 3034 is formed from a polymer configured to expand in response to receipt of the water and/or other physiological fluids. In certain embodiments, the first portions 3032 can be formed from a moisture absorbing, swellable polymer. The second portions 3034 can be formed from a semi-porous film. The first portions 3032 are configured to expand according to a first expansion behavior in response to receipt of a unit volume of fluid. The second portions 3034 can be configured to expand according to a second expansion behavior, different from the first expansion behavior, in response to receipt of the unit volume of fluid. The second portions 3034 can further overlie the first portions 3032 and can be mechanically coupled thereto (e.g., by a biocompatible adhesive or other fixation mechanism). As the second portions 3034 are semi-porous, a portion of the water and/or other physiological fluids received by the second portions 3034 and not absorbed can flow through the second portions 3034 (e.g., via open porosity) for receipt by the first portions 3032.

Figure 17:
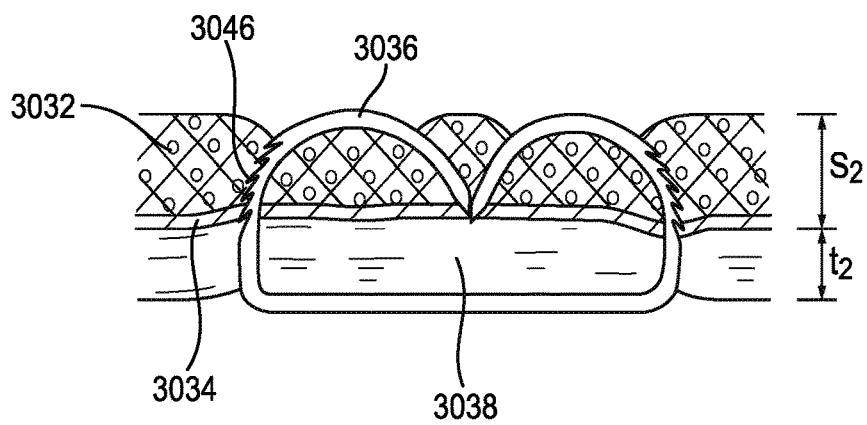
FIG. 17 is a schematic diagram illustrating the stapling assembly and adjunct of FIG. 16 after absorption of water and/or other physiological fluids from the body.

Expansion of the first portions 3032 applies a first pressure (e.g., compressive pressure) to the tissue 3038, and expansion of the second portions, 3034 results in application of second pressure to the tissue 3038. As a result of expansion of the adjunct 3030 and application of pressure by the adjunct 3030 to the tissue 3038, the thickness of the adjunct increases to a third thickness $s_2$ and the thickness $t_2$ of the tissue 3038 decreases, as shown in FIG. 17. In alternative embodiments, the second portion(s) do not substantially expand when receiving water and/or other physiological fluids, or expand to a degree that is significantly less than that of the first portions(s).

In other embodiments, the staples 3036 can include one or more features 3046 configured to permit expansion of the adjunct 3030 in a first direction (e.g., a direction towards the tissue 3038) and to inhibit retraction of the adjunct 3030 in a second direction, opposite the first direction (e.g., a direction away from the tissue 3038). As shown in FIG. 16 and FIG. 17, the one or more features 3046 can include a plurality of barbs extending along one or more of the legs of the staples 3036. The plurality of barbs are positioned such that, after firing into the adjunct, the barbs extend toward the base of the staple, opposite the direction of insertion of the staple into tissue 3038. As the adjunct 3030 expands (e.g., via expansion of the first and/or second portions 3032, 3034), the plurality of barbs engage at least the second portions 3034. As the second portions 3034 are mechanically coupled to the first portions 3032, engagement of the barbs with the second portions 3034 provides a ratcheting-like effect that inhibits retraction of the adjunct 3030 away from the tissue 3038 after expansion of the adjunct 3030.

Embodiments of any portion of any of the adjuncts 3000, 3020, 3030 can be configured to exhibit a change of color in response to expansion. As an example, the portion(s) of the adjuncts 3000, 3020, 3030 exhibiting a color change can include a color transition dye. Examples of the color transition dye can include a hydrochromic ink that is configured to change color in response to at least one fluid, such as water and lipids. In further embodiments, expandable portions of the adjuncts 3030, 3020, 3030 formed from water or lipid sensitive polymers can be in a thin and dry state when un-deployed and expand to a taller state when deployed and hydrated.

The ability of selected portions of the adjuncts 3000, 3020, 3030 to exhibit color change when expanding can allow for rapid, visual identification of expansion behavior. This can be beneficial for confirming that the selected portions of the adjuncts 3000, 3020, 3030 have in fact expanded and therefore, functionality enabled by expansion, such as staple sealing or application of pressure to the cut line is accomplished, without requiring time consuming measurements.

It can be appreciated that such visual identification of the expansion of portions of the adjuncts 3000, 3020, 3030 can be employed for sealing staple It can be appreciated that, because the mass of the portion(s) of the adjuncts 3000, 3020, 3020 exhibiting a color change is constant, the increase in volume resulting from expansion decreases the density of these portions.

Composite Adjuncts that Degrade Through Multiple Different Mechanisms

As discussed above, it can be desirable to employ adjuncts that exhibit compressive properties that degrade as a function of the healing process in order to correlate the amount of compression applied to tissue with that most suitable to facilitate tissue healing. In one aspect, degradation can be correlated to the healing process by use of adjunct materials that degrade in response to reaction with at least one physiological element that is released from tissue during the healing process. In one example, physiological elements including a reactive oxygen species can facilitate degradation by participation in oxidation reactions with the adjunct material. In another example, enzymes released during healing process can catalyze hydrolysis reactions, increasing the rate of degradation of the adjunct material by hydrolysis. This concept can be further employed in the context of composite adjuncts formed from two or more polymers, each of which degrades by a different mechanisms. In this manner, the rate of degradation and attendant change in mechanical properties of the adjunct can be controlled via two mechanisms, rather than a single mechanism, providing greater functionality.

Figure 18:
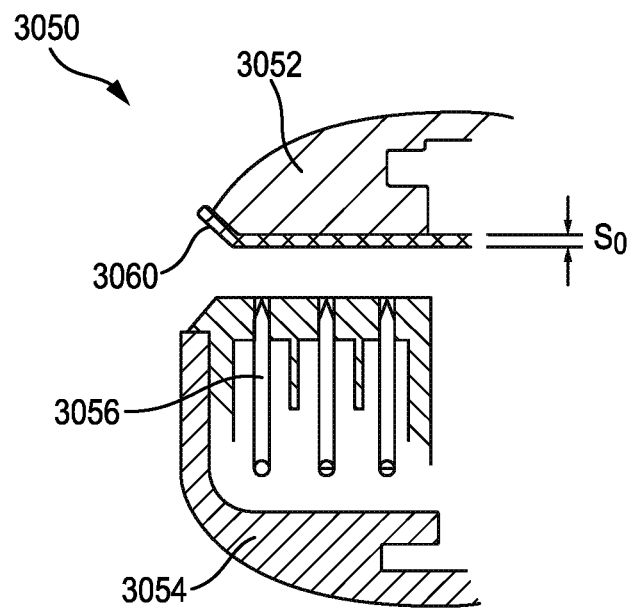
FIG. 18 is a schematic diagram illustrating a side cross-sectional view of a stapling assembly in a pre-firing configuration including an exemplary embodiment of a composite adjunct including first and second polymers.

FIG. 18 is a schematic diagram illustrating a side cross-sectional view of a stapling assembly 3050 in a pre-firing configuration that includes a first jaw having an anvil 3052 opposite a staple cartridge 3054 housing a plurality of staples 3056. As shown, an exemplary embodiment of a composite adjunct 3060 is releasably retained on the anvil 3052 and has a thickness $S_o$. In alternative embodiments (not shown), the composite adjunct 3060 can be releasably retained on either or both of staple cartridge or anvil for delivery to tissue by deployment of staples in the staple cartridge.

Figure 19:
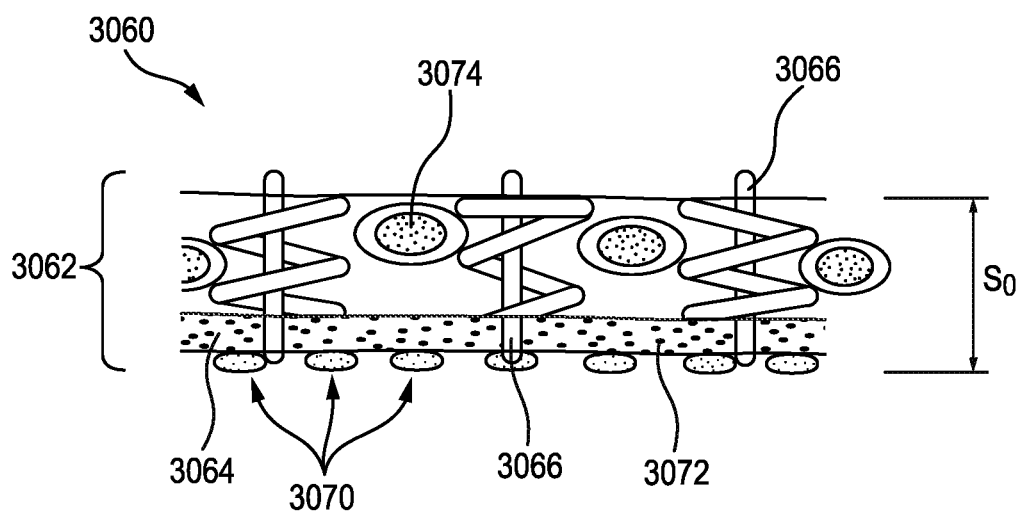
FIG. 19 is a schematic diagram illustrating a side cross-sectional view of the composite adjunct of FIG. 18.

The composite adjunct 3060 is illustrated in greater detail in FIG. 19. The composite adjunct 3060 is formed as a porous polymer body 3062 that includes a first polymer 3064 and a second polymer 3066. The first polymer 3064 overlies the second polymer 3066 and the second polymer 3066 is compressed beneath the first polymer 3064. While first and second polymers 3064, 3066 are shown, the adjunct can include any number of polymers. In certain embodiments, the first polymer 3064 retains at least one first drug 3070 therein. In certain embodiments, the at least one first drug 3070 is a hemostat. In further embodiments, the second polymer 3066 retains at least one second drug 3074 therein configured to encourage tissue remodeling The compression response of the first and second polymers 3064, 3066 and corresponding amount of first and second drugs 3070, 3074 released are illustrated in FIG. 24B and FIG. 24C, respectively, discussed in greater detail below. Healing mechanisms occurring as a function of time are further illustrated in FIG. 24A.

The first polymer 3064 can be configured to degrade according to a first degradation profile as a function of at least one of hydrolysis in response to interaction with water 3072 and heating to a physiological temperature. The first polymer 3064 can further be configured to expand in response to absorption of water 3072 and/or other physiological fluids. Example of the first polymer 3064 include at least one of moisture absorbing powders and moisture absorbing foams.

The second polymer 3066 can be configured to degrade according to a second degradation profile as a function of at least one of oxidation, enzyme-catalyzed hydrolysis, and change of pH resulting from interaction with at least one physiological element 3076 released from the tissue during healing progression of the tissue (FIG. 23), as discussed in greater detail below. The second polymer 3066 is further configured to expand in response to degradation of the first polymer 3064.

Figure 21:
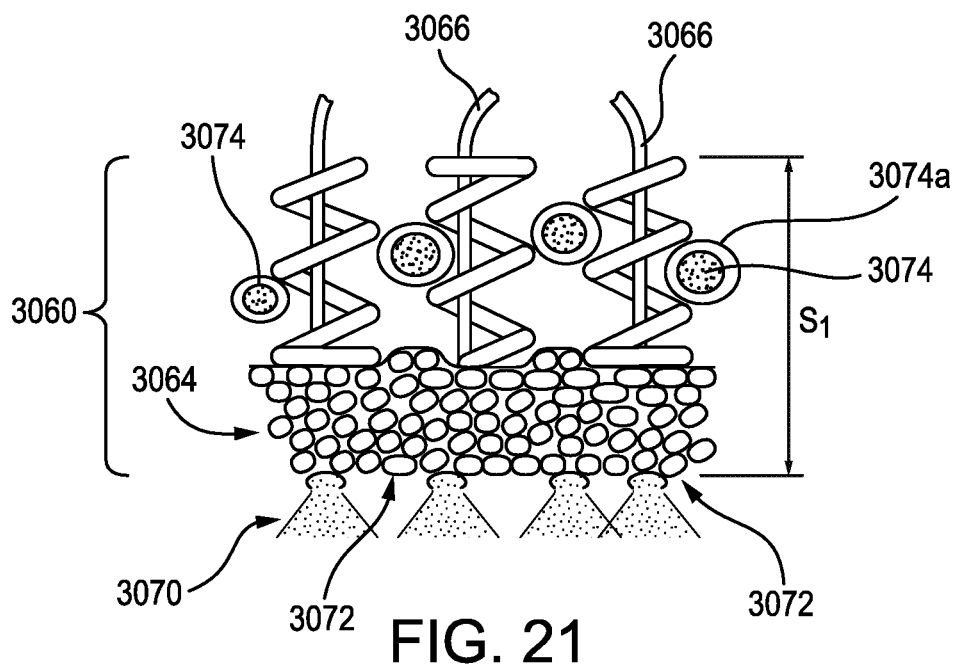
FIG. 21 is a schematic diagram illustrating a magnified side cross-sectional view of the composite adjunct of FIG. 20.

As shown in FIG. 19 and FIG. 21, the first polymer 3064 overlies the second polymer 3064, and therefore mechanically constrains the second polymer 3064. As a result, during the first time window A, the compressive pressure applied by the second polymer 3064 to the tissue 3068 (FIG. 24B) is relatively low and increases relatively slowly as compared to the first polymer 3064. The relatively slow rate of increase of the compressive pressure can be attributed to modest degradation of the first polymer 3064 and attendant relaxation of the constraint of the second polymer 3064.

Examples of the second polymer 3066 include porous structures. Examples of the at least one physiological element can include, but are not limited to, reactive oxygen species. The reactive oxygen species can include at least one of an oxygen containing enzyme, a free radical, a superoxide, and a peroxide.

In certain embodiments, the second polymer 3064 retains the second drug 3074 therein. Examples of the at least one second drug 3074 can include, but are not limited to, drugs configured to promote tissue remodeling. As shown in FIG. 24C, prior to firing (condition time window A, none of the at least one second drug 3074 is released.

In certain embodiments, the at least one second drug 3074 can be configured for at least one of bolus release or gradual release. In one example, as shown in FIG. 21, the second drug 3074 can be encapsulated by a material 3074a that that is configured for gradual release of the second drug 3074 (e.g., a material that degrades relatively slowly in response to interaction with water 3072 and/or other physiological fluids). In another example, graduated release can be provided by one or more relatively large reservoirs formed within the second polymer configured to provide a release of a relatively small volume of the second drug therefrom during a relatively short time period during degradation of the second polymer. As an example, a fluid limiting device, such as a valve, can be employed in combination with a relatively large reservoir for graduated release. In other embodiments, graduated release can be provided by a plurality of relatively smaller volume reservoirs that are configured to independently release relatively small volumes of the second drug over time via degradation of the second polymer (e.g., release of the second drug into respective fluid passageways that are not in fluid communication with one another).

In further embodiments, bolus release of the second drug can be provided by one or more relatively large reservoirs formed within the second polymer that are configured to provide a release of a relatively large volume of the second drug upon during degradation of the second polymer. In alternative embodiments, bolus containment can be provided by a plurality of smaller reservoirs that are configured to concurrently combine respective volumes of the second drug released therefrom during a relatively short time period during degradation of the second polymer (e.g., release of the second drug into one or more common fluid passageways).

Figure 20:
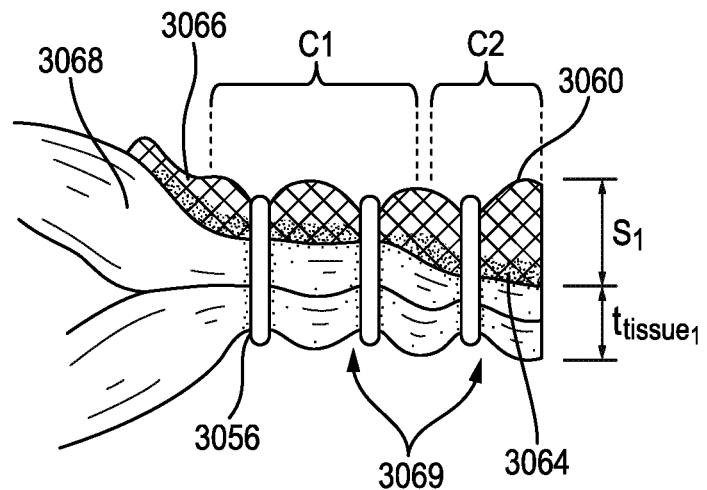
FIG. 20 is a schematic diagram illustrating a side cross-sectional view of the composite adjunct of FIG. 19 coupled to tissue by staples immediately after firing of the stapling assembly.

FIG. 20 is a schematic diagram illustrating the adjunct 3060 immediately after firing the staples 3056 through the adjunct 3060 and tissue 3068 (time window B, FIG. 24A). FIG. 21 is a schematic diagram illustrating the adjunct 3060 in greater detail. As shown, the first polymer 3064 expands in response to interaction with water 3072. As a result of this expansion, the first polymer 3064 exerts a first compressive pressure 3080 on the tissue 3068.

The first degradation profile of the first polymer 3064 during the time window B (FIG. 24A) is a function of interaction (e.g., chemical reaction) with water 3072 (hydrolysis). This configuration can be beneficial for hemostasis, as it results in a first degradation profile that exhibits a relatively rapid rate of decrease of the first compressive pressure 3080 from a peak value. Accordingly, in certain embodiments, a degradation rate of the first polymer 3064 according to the first degradation profile is greater than a degradation rate of the second polymer 3066 according to the second degradation profile.

Concurrently, a release rate 3086 of the first drug 3070 also exhibits a relatively rapid decrease, falling from a maximum value with degradation of the first polymer 3064. That is to say, the at least one first drug 3070 is configured for relatively rapid release. As discussed above, the at least one first drug 3070 can be a hemostat. Accordingly, rapid release of the at least one first drug 3070 can further promote rapid hemostasis.

With compression of the second polymer 3066 beneath the first polymer 3064, the first polymer 3064 can constrain expansion of the second polymer 3066. This is reflected in FIG. 24B as a relatively slow rate of increase of the second compressive pressure 3082. However, the ability of the first polymer 3064 to constrain the second polymer 3066 diminishes with continued degradation of the first polymer 3064, and the rate of increase of the second compressive stress 2412 on the tissue 3068 rises as time progresses within the second time window B. As a result, the thickness of the adjunct 3060 can increase from an initial thickness $S_o$ to a first thickness $S_1$. The tissue thickness has an initial thickness $t_{tissue1}$. The combination of the first and second compressive pressure 3080, 3082 further promotes hemostasis, providing a region 3069 of restricted blood flow for clotting.

In certain embodiments, at least one of the first polymer and the second polymer can include a hydrogel that is configured to expand by a larger amount than the surrounding polymer material. In this way, the resulting composite adjunct can exhibit varying amounts of expansion. In this manner, different levels of compression can be applied by the adjunct to different regions of the tissue (e.g., cut line, staple line, etc.) As shown in FIG. 20, the composite adjunct 3060 applies two different levels of compression C1 and C2 at different regions. For example, the compression C2 can be greater than the compression C1 and positioned proximate to a cut line to thereby increase local pressure to seal the region until healing.

As healing progresses during the second time window B (e.g., the inflammation phase and release of neutrophils), the concentration of the at least one physiological element 3076 received at the composite adjunct 3060 increases. As an example, neutrophils can be released, along with corresponding ones of the at least one physiological element 3076. Concurrently, degradation of the first polymer 3064 progresses with time, reducing the ability of the first polymer 3064 to inhibit interaction of the second polymer 3066 with the at least one physiological element 3076. Thus, the rate of degradation of the second polymer 3066 increases, reflected as an increase in release rate 2086 of the at least one second drug 3074 from the second polymer 3066 as time progresses within the second time window B.

Figure 22:
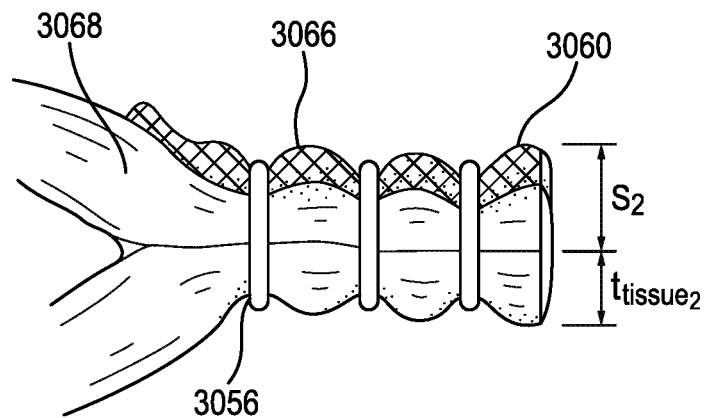
FIG. 22 is a schematic diagram illustrating a side cross-sectional view of the composite adjunct of FIG. 19 coupled to tissue by staples at a predetermined time duration after firing of the stapling assembly.
Figure 23:
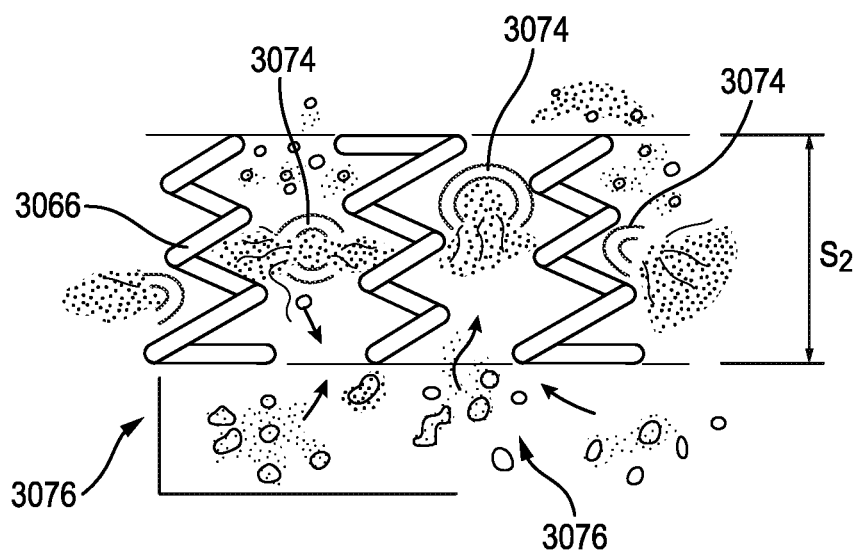
FIG. 23 is a schematic diagram illustrating a side cross-sectional view of the composite adjunct of FIG. 22.

FIG. 22 is a schematic diagram illustrating the adjunct 3060 at a predetermined time after firing the staples 3056 through the adjunct 3060 and tissue 3068 (time window C, FIG. 24C). FIG. 23 is a schematic diagram illustrating the adjunct 3060 in greater detail. As shown, degradation of the first polymer 3064 is substantially complete, by the relatively low magnitude of the first compressive pressure 3080, and relatively low release rate 3084 of the at least one first drug 3070. That is, substantially all of the at least one first drug 3070 has been released. Furthermore, due to the reduction in the first compressive pressures 3080, the thickness of the adjunct 3060 decreases from the first thickness $S_1$ to a second thickness $S_2$ and the thickness of the tissue 3068 increases from an initial tissue thickness $t_{tissue1}$ to a second tissue thickness $t_{tissue2}$. Beneficially, the combination of first and second compressive pressures 3080, 3082 applied to the tissue 3068 are at a level sufficient to allow vascularization.

Concurrently, healing continues to progress from the inflammation to the proliferation and maturation stages, resulting in release of macrophages, fibroblasts, and lymphocytes, as illustrated in FIG. 24A and corresponding ones of the at least one physiological element 3076. With the high degree of degradation of the first polymer 3064 during time window C, the ability of the at least one first polymer 3064 to inhibit interaction of the second polymer 3066 with the at least one physiological element 3076 is significantly reduced. Thus, the at least one physiological element 3076 can freely flow into the pores of the second polymer 3066. This increases the degradation rate of the second polymer 3066, decreasing the second compressive pressure 3082.

The release rate 3086 of the at least one second drug increases to a peak with increasing degradation of the second polymer 3066, then decreases from the peak. The relatively slow release of the at least one second drug 3074 can encourage tissue remodeling. Examples of drugs configured to encourage tissue remodeling can include drugs that are configured to treat pain or inflammation. Further examples of such drugs can include, but are not limited to, MMP inhibitors. Examples of MMP inhibitors can be found in U.S. Pat. Nos. 10,939,911 and 10,569,071 and U.S. Patent Publication Nos. 2018/0353659, 2018/0353175, and 2018/0353174, each of which is incorporated by reference in their entirety.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A compressible adjunct for use with a staple cartridge, the compressible adjunct comprising:
a biocompatible adjunct material configured to releasably retained on a staple cartridge body and configured to be delivered to tissue by deployment of staples in the staple cartridge body, the adjunct material comprising a porous polymer body configured to exhibit a first stiffness in compression that is approximately constant during a first time period from contact with the tissue and to exhibit a second stiffness in compression during a second time period following the first time period, wherein the second stiffness is less than the first stiffness and is configured to decrease with time as a function of at least one of oxidation, enzyme-catalyzed hydrolysis, and change of pH resulting from interaction with at least one physiological element released from the tissue during healing progression of the tissue.

2. The adjunct of claim 1, wherein the adjunct material is configured to adopt the second stiffness in response to oxidation resulting from reaction with the at least one physiological element comprising a reactive oxygen species.

3. The adjunct of claim 2, wherein the reactive oxygen species is at least one of an oxygen containing enzyme, a free radical, a superoxide, and a peroxide.

4. The adjunct of claim 2, wherein the reactive oxygen species is at least one of $O^{2-}$, $H_2O_2$, NO, and HOCl.

5. The adjunct of claim 1, wherein the adjunct material is configured to oxidize in response to reaction with the at least one physiological element comprising a reactive oxygen species released by at least one of a mature blood cell, a fybrocyte, and an inflammatory cell.

6. The adjunct of claim 5, wherein the inflammatory cell is at least one of a leukocyte and a macrophage.

7. The adjunct of claim 1, wherein the adjunct material is configured adopt the second stiffness in response to hydrolysis catalyzed by an enzyme.

8. The adjunct of claim 7, wherein the enzyme comprises a lysozyme.

9. The adjunct of claim 1, wherein adjunct material is configured to adopt the second stiffness in response to a decrease in pH resulting from the presence of the at least one physiological element.

* * * * *